United States Patent
Kobayashi et al.

(10) Patent No.: US 7,034,932 B2
(45) Date of Patent: Apr. 25, 2006

(54) DEPOSIT DETECTOR AND CONTROLLER USING THE DETECTOR

(75) Inventors: Fumitoshi Kobayashi, Osaka (JP); Keiji Tsunetomo, Osaka (JP); Hideki Imanishi, Osaka (JP); Harunobu Yoshida, Osaka (JP); Masahide Wakisaka, Osaka (JP); Tatsumi Tokuda, Osaka (JP)

(73) Assignee: Niles Co., Ltd., Tokyo (JP)

( * ) Notice: Subject to any disclaimer, the term of this patent is extended or adjusted under 35 U.S.C. 154(b) by 313 days.

(21) Appl. No.: 10/363,583

(22) PCT Filed: Sep. 7, 2001

(86) PCT No.: PCT/JP01/07809

§ 371 (c)(1), (2), (4) Date: May 3, 2003

(87) PCT Pub. No.: WO02/21107

PCT Pub. Date: Mar. 14, 2002

(65) Prior Publication Data

US 2003/0183752 A1   Oct. 2, 2003

(51) Int. Cl.
*G01N 21/17* (2006.01)

(52) U.S. Cl. ............. 356/239.8; 356/445; 318/DIG. 2; 250/227.25

(58) Field of Classification Search ............. 356/445, 356/239.8; 250/227.25; 318/DIG. 2
See application file for complete search history.

(56) References Cited

U.S. PATENT DOCUMENTS

| | | | | |
|---|---|---|---|---|
| 4,676,638 A | * | 6/1987 | Yasuda | 356/239.8 |
| 4,867,561 A | * | 9/1989 | Fujii et al. | 356/239.8 |
| 5,666,037 A | * | 9/1997 | Reime | 318/DIG. 2 |
| 5,808,734 A | * | 9/1998 | Kolari | 318/DIG. 2 |

FOREIGN PATENT DOCUMENTS

| | | |
|---|---|---|
| JP | 63-94135 | 4/1988 |
| JP | 2-162245 | 6/1990 |

* cited by examiner

*Primary Examiner*—Richard A. Rosenberger
(74) *Attorney, Agent, or Firm*—Hamre, Schumann, Mueller & Larson, P.C.

(57) ABSTRACT

The present invention provides an object-sensing device capable of estimating the presence of an object attached on a sensing surface, the kind of the object and the state of the object. An image is formed by a lens with light via the sensing surface, and the light is received by a light-receiving element portion in which a plurality of micro-light-receiving elements are arranged. In the object detection mode, totally reflected light from the sensing surface is received by the light-receiving element portion. The components are arranged at an angle that allows total reflection when there is no object, and does not allow the total reflection condition to be satisfied when there is an object. In the light scattering object detection mode, scattered light from the sensing surface is received by the light-receiving element portion. A signal pattern is obtained by joining detection signal levels of the micro-light-receiving elements in accordance with the arrangement of the micro-light-receiving elements. An increase portion or a drop portion of the signal pattern that appears in accordance with the presence of the object or a difference in the state thereof is analyzed, so that the kind and the state of the object such as a rain drop, muddy water, fogging, ice or the like are estimated.

15 Claims, 23 Drawing Sheets

| | (1) | (2) | (3) | (4) | (5) |
|---|---|---|---|---|---|
| Object sensor operation mode | Signal level no change | Signal level drop | Signal level drop | Signal level drop (small drop ratio) | Signal level increase |
| Light scattering object sensor operation mode | Signal level no change | Signal level no change (near 0 level) | Signal level increase (large increase ratio) | Signal level increase (small increase ratio) | Signal level drop |
| Estimation results | no object or no change in object state | substance without light scattering properties attached (rain drop attached) | substance with light scattering properties attached (muddy water having water content attached) | substance with light scattering properties attached (dry muddy water attached) | Object removed |

FIG.8

| | (1) | (2) | (3) | (4) | (5) | (6) |
|---|---|---|---|---|---|---|
| Object detection mode | Signal pattern no change | Signal pattern drop portion | Signal pattern drop portion (large drop ratio) | Signal pattern drop portion (small drop ratio) | Signal pattern no change (drop as a whole) | Signal pattern irregular change (drop as a whole) |
| Light scattering object detection mode | Signal pattern no chang | Signal pattern no change | Signal pattern increase portion (large increase ratio) | Signal pattern increase portion (small increase ratio) | Signal pattern no change (increase as a whole) | Signal pattern irregular change (increase as a whole) |
| Estimation results | no object or object removed | substance without light scattering properties attached (rain drop attached) | substance with light scattering properties attached (muddy water having water content attached) | substance with light scattering properties attached (dry muddy water attached) | fogging due to condensation | frozen deposit |

FIG.19

DEPOSIT DETECTOR AND CONTROLLER USING THE DETECTOR

TECHNICAL FIELD

The present invention relates to an object-sensing device for detecting the presence of an object attached on a sensing surface, the properties of the object, and the state of the object, and a control device using the object-sensing device for changing a control in response to a detection of the presence of the object by the object-sensing device.

BACKGROUND ART

There are various systems for detecting whether or not an object is present and changing a control in response to a detection of the presence of the object. Taking rain drops as an example of the object, a windshield wiper control device of a windshield of an automobile has to change a control flexibly in response to a weather change leading to the start of rainfall. Development of a rain sensor for detecting whether or not it is raining is an important issue to enhance the convenience of a windshield wiper control device. Hereinafter, a conventional object-sensing device will be described by taking as an example a conventional rain sensor for detecting rain drops on a windshield of an automobile as an object.

In the case of a windshield wiper operated manually, which commonly is used, drivers have to recognize that it started to rain and manually switch a windshield wiper from off to on in view of the running state of the automobile and a change in the amount of rain drops attached on the windshield in order to ensure a necessary view through the windshield for driving the automobile. In order to reduce the trouble of this manual switching operation of the windshield wiper, a rain sensor is provided to detect the presence of an object such as rain drops on a sensing surface of the windshield of an automobile so as to determine whether or not the windshield needs wiping.

As a conventional rain sensor, rain sensors employing reflected light to detect rain drops are known. FIG. 23 shows a view simply illustrating the principle of detecting rain drops by a conventional reflected light sensing type rain sensor. In FIG. 23, reference numeral 1000 denotes a windshield of an automobile. For convenience, the upper space of the windshield 1000 is inside of the automobile, that is, the space on the side of a driver, and the lower space is outside of the automobile. Reference numeral 1010 denotes a light source, 1020 denotes a prism, 1030 denotes a prism for guiding reflected light out from the inner portion of the windshield, 1040 denotes a lens, 1050 denotes a PD (Photo Detector) as a light-receiving element, and 1110 denotes a sensing surface. Reference numeral 1120 denotes a rain drop on the sensing surface. The light source 1010 irradiates light flux spread widely enough to cover the entire sensing surface, and among the light flux, 1130 denotes a locus of the light incident to a portion in which the rain drop is attached. Reference numeral 1140 denotes a locus of light other than the light 1130, which is incident to a portion of the sensing surface on which the rain drop is not attached.

In the reflected light sensing type rain sensor, it is important to adjust the angle at which each component is provided and the material thereof (in particular, the refractive index of the material). Describing the basic principle of detecting rain drops, when a rain drop is on a sensing surface, incident light escapes to the outside because a total reflection condition is not satisfied in the external surface of the windshield 1000. On the other hand, when a rain drop is not attached on a sensing surface, the total reflection condition is satisfied in the external surface of the windshield 1000 and incident light is reflected totally. The reflected light sensing type rain sensor detects a difference in the intensity of the reflected light in these two cases.

Therefore, for the light source 1010 and the prism 1020, the angles and the materials are selected so as to satisfy the incident condition under which irradiated light is incident to the inner portion of the windshield 1000. In addition, an angle that allows total reflection in the sensing surface on the external surface of the windshield 1000 is selected. Furthermore, an angle at which light is incident with respect to the sensing surface 1110 is selected so that the total reflection condition on the sensing surface is switched so as to be satisfied or not satisfied in response to a change of the refractive index due to rain drops.

For the prism 1030, the material and the angle are selected so as to satisfy an outgoing condition under which reflected light can exit from the windshield 1000, that is, so as not to satisfy the total reflection condition. For the lens 1040 and the light-receiving element 1050, the angles and the distance are adjusted such that light incident to the lens 1040 is focused on the sensor portion of the light-receiving element 1050.

These components 1010 to 1050 can be provided on places other than the windshield 1000, for example, on the hood or the roof. However, since the state of the windshield 1000 is to be detected, it is preferable to provide these components in a portion of the windshield 1000. It is also preferable to provide these components so as not to hinder the view of a driver. For example, it is preferable to provide these components in a portion of the windshield in which the view originally is shielded by a rearview mirror.

The operation of the above-described conventional reflected light sensing type rain sensor will be described below. The light flux irradiated from the light source 1010 is admitted to the internal portion of the windshield 1000 by the prism 1020 and is incident onto the entire surface of the sensing surface 1110. Now, it is assumed that a rain drop 1120 is attached on the sensing surface 1110. Among the light incident on the sensing surface 1110, the light 1130 that has been incident to the portion in which the rain drop 1120 is attached escapes to the outside because the total reflection condition is not satisfied because of the rain drop having a refractive index n of about 1.3 on the external surface of the windshield 1000, and this light is not detected by the light-receiving element 1050. On the other hand, among the light incident to the sensing surface 1110, the light 1140 that has been incident on a portion to which the rain drop is not attached is totally reflected because the total reflection condition is satisfied because of the air having a refractive index n of about 1 on the external surface of the windshield 1000. The totally reflected light is not totally reflected due to the presence of the prism 1030 on the surface of the windshield 1000 inside of the automobile and exits to the interior of the automobile. The light that has exited is focused on the photosensor portion on the light-receiving element 1050 by the lens 1040.

Thus, the amount of light detected by the light-receiving element 1050 decreases when the rain drop 1120 is present, and the larger the area of the sensing surface 1110 that is covered with the rain drop 1120 becomes, the less the amount of light detected becomes. This change of the light amount is detected to determine the presence of the rain drop on the sensing surface 1110. The above is the principle of the rain drop detection by the conventional reflected light sensing type rain sensor.

Each type of a rain sensor is configured so as to output a rain drop detection signal when a signal change as described above is detected. The rain drop detection signal from the rain sensor is input to a control portion of a windshield wiper, and the windshield wiper is controlled as desired in response to the input of the rain drop detection signal.

However, the conventional rain sensor has the following problems.

A first problem is that although the presence of an object can be detected with the conventional rain sensor, the type of the object and the state are not estimated. The main purpose of the rain sensor is to control the driving of the wiper that wipes the windshield 1000, if necessary, and there are some cases where the driving of the wiper has to be switched in accordance with the type and the state of an object attached on the windshield 1000. The conventional rain sensor cannot estimate the type of the object and the state thereof, so that it cannot but perform the same and uniform control.

The object attached on the windshield 1000 is not necessarily water drops due to rainfall. Various kinds of objects can be thought of, such as muddy water scattered during driving and droppings dropped by birds such as pigeons. The state of the object is varied, and even when water is attached, various states can be thought of, such as in the state of fogging on the windshield, or in the state of frozen ice caused by temperatures dropping in winter. In the case of muddy water, there are a state with a large water content and a dry state with a small water content. Also in the case of droppings of birds, there are soft droppings and dry droppings.

It is preferable to switch the driving of the wiper in accordance with the type and the state of the object attached on the windshield 1000. For example, when water is frozen, or when muddy water or droppings of birds are dry, wiping only with a wiper is not effective, and what is worse, the device or the windshield may be damaged. In this case, for example, it is preferable to drive the wiper while spraying cleaning liquid.

A second problem is concerned with the precision of object detection. In the conventional rain sensor, an absolute value of a signal level of the amount of light detected by the light-receiving element is analyzed, or signal levels detected at a constant time interval are stored, and temporal changes of the signal levels are analyzed so as to detect the presence of an object on the sensing surface. The temporal changes of the detected signal levels are slightly different, depending on the type of the object and the object state, but it is not easy to detect such a slight change precisely and estimate the type of the object and the object state.

DISCLOSURE OF INVENTION

In view of the above-described problems, it is an object of the present invention to provide an object-sensing device for not only detecting the presence of an object on a sensing surface, but also estimating the kind of the object and further estimating the state thereof, and a control device for performing control in accordance with the kind and the state of the object that are estimated with the object-sensing device.

In order to solve the above problems, a first object-sensing device of the present invention includes a light source for total reflection and a light source for scattering, and an outer surface of a transparent substrate is used as a sensing surface on which an incident light admitted into the transparent substrate from the light source for total reflection is reflected, and an incident light admitted into the transparent substrate from the light source for scattering is irradiated. The light source for total reflection, the transparent substrate and a light receiver are arranged such that the reflected light of the light source for total reflection from the sensing surface can be received by the light receiver, and the light source for scattering and the light receiver are arranged such that scattered light of the light source for scattering from the sensing surface can be received by the light receiver. The object-sensing device includes an object sensor for detecting a change in a signal level from the light source for total reflection due to an object in a photo detection signal detected by the light receiver so as to detect the presence of the object; and a light-scattering-object sensor for detecting a change in a signal level from the light source for scattering due to an object in a photo detection signal detected by the light receiver so as to detect whether or not the object is a light scattering object.

With this feature, not only the presence of an object based on a change in the reflection condition by the object sensor, but also the presence of a light scattering object based on a change in the scattering condition by the light-scattering-object sensor can be detected, and the kind of the object can be estimated based on the light scattering properties of the object.

In the first object-sensing device, it is preferable that the object sensor and the light-scattering-object sensor receive light from the same detecting surface.

According to this feature, the sensing surface can be used as a common surface for the two detectors, so that the device can be small.

In the first object-sensing device, it is preferable that the object-sensing device operates while switching the light source for total reflection and the light source for scattering.

According to this feature, even if the two detectors use a common sensing surface, the two detectors can be controlled easily.

Next, in the first object-sensing device, it is preferable that when the presence of an object is detected by the object sensor, and the presence of a light scattering object is detected by the light-scattering-object sensor, then the object is estimated to be a substance having light scattering properties, and when the presence of an object is detected by the object sensor, and the presence of a light scattering object is not detected by the light-scattering-object sensor, then the object is estimated to be a substance having light transmission properties. In other words, it is preferable that when the presence of an object is detected by the object sensor, and the presence of a light scattering object is detected by the light-scattering-object sensor, then the object is estimated to be muddy water, and when the presence of an object is detected by the object sensor, and the presence of a light scattering object is not detected by the light-scattering-object sensor, then the object is estimated to be a water drop.

With this feature, it can be estimated whether a detected object is a substance having light scattering properties with little light transmission properties, for example, mud, or a substance having light transmission properties, for example, a rain drop. This is because muddy water has light scattering properties, so that light scattering occurs on the sensing surface, whereas rain drops are transparent and do not have light scattering properties, so that light scattering does not occur on the sensing surface.

In order to solve the above problems, a second object-sensing device of the present invention includes two types of light sources for total reflection and scattering. A portion of an outer surface of a transparent substrate is used as a sensing surface on which an incident light admitted into the transparent substrate from the light source for total reflection is reflected, and an incident light admitted into the transparent substrate from the light source for scattering is irradiated. The object-sensing device includes an imaging lens for forming an image with each of the reflected light by the light source for total reflection and scattered light by the light source for scattering that are incident from the sensing surface, and a light-receiving element array. Light from the imaging lens is received, and a signal pattern in which photo detection signals from each micro-light-receiving element are aligned in accordance with an arrangement of the micro-light-receiving elements is generated for each light source, and the signal pattern corresponding to an object state of an object on the sensing surface is output.

With this feature, not only the presence of an object based on a change in the reflection condition by the object sensor, but also the presence of scattering properties of the object based on a change in the scattering condition by the light-scattering-object sensor can be detected, and the kind of the object can be estimated based on the scattering properties of the object. With this feature, one kind of signal pattern (signal waveform) in which photo detection signals detected from micro-light-receiving elements corresponding to the sensing surface are aligned in accordance with the arrangement of the light-receiving elements can be obtained. This signal pattern is obtained by joining signal levels obtained from the sensing surface so as to form a pattern, and a difference in the state of the object on the sensing surface is indicated by a relative change between micro-sections of the signal pattern. The present invention can estimate, for example, the kind and the state of the object on the sensing surface by analyzing the relative change in the signal pattern. Furthermore, since the relative change between the micro-sections of the signal pattern is analyzed, the presence of a fine object can be detected with high precision, and the detection hardly is affected by a change in the surroundings due to the temperature characteristics. The resolution of this signal pattern depends on the light-receiving elements corresponding to the sensing surface.

It is preferable that the second object-sensing device includes a light switch for switching irradiation of the light source for total reflection and irradiation of the light source for scattering.

With this feature, a signal pattern can be obtained with the light source for total reflection in distinction from a signal pattern with the light source for scattering. It is preferable to switch the light source for total reflection and the light source for scattering so as not to be mixed, in particular, when the light source for total reflection and the light source for scattering have the same wavelength.

Next, it is preferable that the second object-sensing device includes an object sensor for detecting that an object is present when the presence of a pattern portion in which a signal level drops relative to neighboring signal levels is detected in the signal pattern, the object being present on the sensing surface corresponding to the pattern portion; and a light-scattering-object sensor for detecting that a light scattering object is present when the presence of a pattern portion in which a signal level increases relative to neighboring signal levels is detected in the signal pattern, the light scattering object being present on the sensing surface corresponding to the pattern portion, and that when the presence of the object is detected by the object sensor, and the presence of the light scattering object is detected by the light-scattering-object sensor, then the object is estimated to be a substance having light scattering properties, and when the presence of the object is detected by the object sensor, and the presence of the scattering object is not detected by the light-scattering-object sensor, then the object is estimated to be a substance having light transmission properties.

With this feature, it can be estimated whether the detected object has scattering properties with little light transmission properties or has light transmission properties.

Furthermore, it is preferable that in the second object-sensing device, the magnitude of the light scattering properties of the object is estimated based on a relative magnitude of a pattern portion exhibiting a relative increase from neighboring signal levels in the signal pattern of the scattered light of the light source for scattering that is detected by the light-scattering-object sensor.

With this feature, the magnitude of the light scattering properties of the object can be estimated in view of a relative change in the signal pattern.

Furthermore, it is preferable that in the second object-sensing device, the kind and the state of the object are estimated based on a relative change of a pattern portion exhibiting a relative increase from neighboring signal levels in the signal pattern of the scattered light of the light source for scattering that is detected by the light-scattering-object sensor.

With this feature, the kind and the state of the object can be estimated accurately in view of a relative change in the signal pattern.

Furthermore, in the second object-sensing device, when the presence of an object is detected by the object sensor, and the presence of a scattering object is detected by the light-scattering-object sensor, then the object can be estimated to be muddy water, and when the presence of an object is detected by the object sensor, and the presence of a scattering object is not detected by the light-scattering-object sensor, then the object can be estimated to be a water drop.

This is because muddy water has light scattering properties, so that light scattering occurs in the sensing surface, whereas rain drops are transparent and do not have light scattering properties, so that light scattering does not occur.

Furthermore, in the second object-sensing device, when the presence of an object is detected by the object sensor, and the presence of a scattering object is detected by the light-scattering-object sensor, then the object can be estimated to be muddy water, and a relative magnitude of a pattern portion exhibiting a relative increase of a signal level from neighboring signal levels in the signal pattern of the scattered light of the light source for scattering that is detected by the light-scattering-object sensor is smaller than a predetermined ratio, then it can be estimated that the muddy water is dry.

This is because dry mud is in contact with the sensing surface only at its contact point in a microscopic view, so that the region in which light scattering occurs is relatively smaller than in the case of muddy water and the ratio of the relative magnitude of the signal drop portion in the signal pattern becomes small.

Furthermore, in the second object-sensing device, when in a signal pattern of the reflected light of the light source for total reflection detected by the object sensor a signal level drop throughout the signal pattern is detected, and in a signal pattern of the scattered light of the light source for scattering detected by the light-scattering-object sensor a signal level increase throughout the signal pattern is detected, then the object can be estimated to be water droplets due to condensation.

This is because condensed dews are attached so as to cover the entire sensing surface, and the entire signal level is changed, and there is not a large difference on the sensing surface so that the signal pattern is smooth.

Furthermore, in the second object-sensing device, when in a signal pattern of the reflected light of the light source for total reflection detected by the object sensor, a signal level drops over the signal pattern and a change in the signal pattern is not smooth, and in a signal pattern of the scattered light of the light source for scattering detected by the light-scattering-object sensor a signal level is increased over the signal pattern and a change in the signal pattern is not smooth, then the object can be estimated to be ice due to freezing.

This is because when ice is present, the ice covers the entire sensing surface, and the entire signal level is changed, and a difference in the state on the sensing surface is created in an irregular manner because of a complex change of the shape of the surface of ice, so that irregularity can be seen in the signal pattern.

Next, the object-sensing device of the present invention described above can be used as a rain sensor for detecting the presence of an object attached on a windshield by providing the sensing surface on the windshield of an automobile. A windshield wiper device can be configured by using the object-sensing device as a rain sensor and further including a windshield wiper driver; and a windshield wiper controller. The windshield wiper controller changes the control method of the windshield wiper driver, based on estimation results with respect to the kind and the state of an object from the object-estimating portion.

With this feature, a windshield wiper device in which the wiping control of the wiper is controlled so as to be appropriate in accordance with the presence, the kind, and the state of the object on the windshield can be provided. For example, when rain drops are detected, the wiper is put in wiping mode. When muddy water having a water content is detected, also the wiper is put in wiping mode. When dry mud is detected, also the wiper is not put in wiping mode but in operation of spaying washer liquid. When condensed dew (so-called fogging) is detected on the sensing surface, the wiper is put in wiping mode. When ice is detected on the sensing surface, a process appropriate to the state of the sensing surface is employed, such as start of a heater for preventing freezing without putting the wiper in wiping mode or spraying washer liquid.

BRIEF DESCRIPTION OF DRAWINGS

FIG. 8 is a view showing an estimation of the presence of an object, the kind of the object and the state of the object with photo detection signal levels in an object detection mode and a light scattering object detection mode of the first object-sensing device of the present invention.

FIG. 19 is a view showing an estimation of the presence of an object, the kind of the object and the state of the object with photo detection signal levels in an object detection mode and a light scattering object detection mode of the second object-sensing device of the present invention.

BEST MODE FOR CARRYING OUT THE INVENTION

Figure 1A:
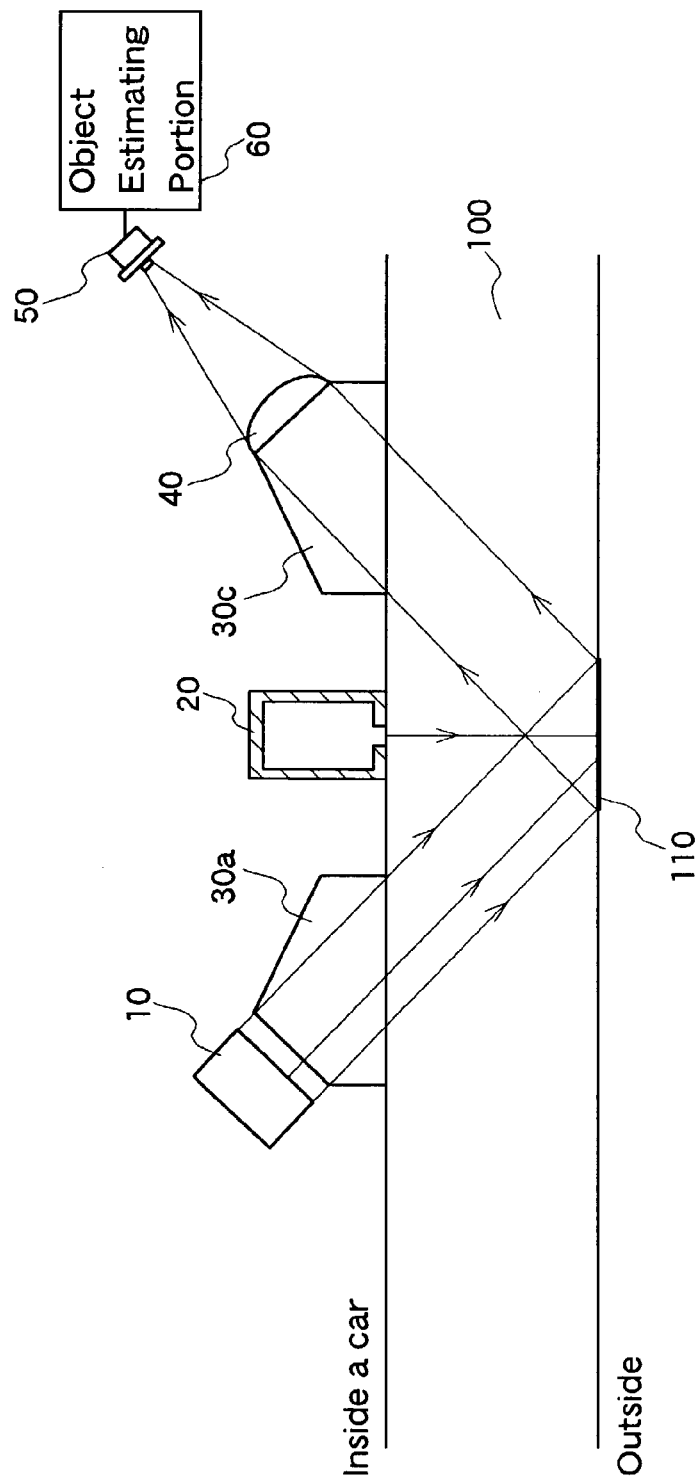
FIG. 1 is a schematic view simply showing an example of a device configuration of a first object-sensing device of the present invention.

In Embodiments 1 and 2, an object-sensing device for estimating an object by the level of a photo detection signal of an incident light obtained in a light-receiving element through a sensing surface will be described as a first object-sensing device of the present invention.

In Embodiments 3 to 6, an object-sensing device for estimating an object by using a micro-light-receiving element array in which a plurality of micro-light-receiving elements are aligned as the light-receiving element, and analyzing a signal pattern obtained by joining photo detection signal levels of an incident light obtained in each micro-light-receiving element through a sensing surface will be described as a second object-sensing device of the present invention.

Furthermore, in Embodiment 7, a windshield wiper control device using the object-sensing device of the present invention as a rain sensor will be described.

(Embodiment 1)

The first object-sensing device of the present invention will be described. An object-sensing device capable of estimating the presence of an object on a sensing surface and whether or not the object is a substance having light scattering properties will be described as Embodiment 1. In particular, taking as an example the case where the object is a rain drop and is muddy water, it is described that the former and the latter can be distinguished.

The basic principle of the object-sensing device of Embodiment 1 of the present invention is as follows. A reflected light from a light source for total reflection and scattering light from a light source for scattering light that are irradiated onto a sensing surface are received by a light receiver, and the levels of photo detection signals are analyzed so that a change in the total reflection condition and the scattering condition on the sensing surface due to the presence, the kind and the state of the object on the sensing surface is detected, so that the presence, the kind and the state of the object are estimated.

The object-sensing device of the present invention has a configuration, for example, where an object detection mode using a light source of total reflection and a light scattering object detection mode using a light source for scattering, which are described below, are provided in order to estimate the presence, the kind and the state of the object on the sensing surface of a transparent substrate. Alternatively, a configuration without the object detection mode and only with the light scattering object detection mode, or a configuration without the light scattering object detection mode and only with the object detection mode can be configured as alternative embodiments.

Herein, the "object detection mode" refers to a mode for detecting the presence of an object on the sensing surface of a transparent substrate. The "light scattering object detection mode" refers to a mode for detecting whether the object on the sensing surface has light scattering properties, for example, whether the object is muddy water or droppings of birds, etc., which have light scattering properties. In the object-sensing device of the present invention, the presence of the object on the sensing surface is detected in the object detection mode, and when the light scattering properties are not detected in the light scattering object detection mode, it is estimated that the object is a rain drop, etc. that has light transmission properties. Furthermore, the presence of the object on the sensing surface is detected in the object detection mode, and when the light scattering properties are detected in the light scattering object detection mode, it is estimated that the object is muddy water, etc. that has light scattering properties.

FIG. 1 is a simplified schematic view showing an example of a device configuration of the object-sensing device of the present invention of Embodiment 1.

In FIG. 1, reference numeral 100 denotes a windshield 100 as an example of a transparent substrate. The layer below the windshield 100 is the outside. A sensing surface 110 is in a predetermined region on a boundary surface between the windshield 100 and the outside. Reference numeral 10 denotes a light source for total reflection, and reference numeral 20 denotes a light source for scattering. Reference numerals 30a and 30c are prisms. Reference numeral 40 denotes a condenser lens, and reference numeral 50 denotes a light-receiving element portion as a light receiver. Reference numeral 60 denotes an object-estimating portion. In this example, the light source 10 for total reflection, the prisms 30a and 30c, the condenser lens 40, and the light-receiving element portion 50 constitute an object sensor. The light source 20 for scattering, the prism 30c, the condenser lens 40, and the light-receiving element portion 50 constitute a light-scattering-object sensor.

Figure 1C:
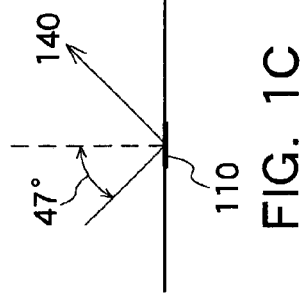
Figure 1B:

The light source 10 for total reflection can irradiate a directional irradiation light and is disposed at a position and an angle that allow the irradiation light to be incident at a predetermined angle with respect to the sensing surface 110. The light source for total reflection is adjusted such that the light emitted from the light source 10 for total reflection and admitted the windshield 100 via the prism 30a is incident to the sensing surface 110, and the total reflection condition on the sensing surface is satisfied when there is no object on the sensing surface 110, as shown in FIG. 1(c), that is, air is in contact. The prism 30c, the condenser lens 40, and the light-receiving element portion 50 are adjusted such that the reflected light that is totally reflected into the windshield 100 at the sensing surface 110 is emitted outside the windshield 100 via the prism 30c provided on the surface of the windshield 100, and is focused on the light-receiving surface of the light-receiving element portion 50 by the condenser lens 40. The angles at which the light source 10 for total reflection and the above-described components are provided are adjusted such that the total reflection condition on the sensing surface 110 is not satisfied when a rain drop (water content) is in contact as shown in FIG. 1B.

The total reflection condition is represented by Formula 1.

Formula 1

$$\theta_1 > \sin^{-1}\left(\frac{n_1}{n_2}\right)$$

where $n_1$ is the refractive index of outside material, $n_2$ is the refractive index of the windshield 100, and $\theta_1$ is the angle at which the irradiation light is incident to the sensing surface.

Herein, when $n_1$, which is the refractive index of air, that is, outside material when no rain drop is present, as shown in FIG. 1(c), is 1, and $n_2$, which is the refractive index of the windshield 100, is about 1.51, for example, then Formula 1 results in 41.47°<$\theta_1$. Furthermore, when a rain drop is attached as shown in FIG. 1B, the refractive index of water is about 1.33, so that $\theta_1$<61.74° is sufficient. In other words, the light incident angle $\theta_1$ that switches whether the total reflection condition shown in Formula 1 on the sensing surface 110 is satisfied or not satisfied is selected from the range of 41.47°<$\theta_1$<61.74°. In this example, the arrangement of the components and the angles at which the components are provided are adjusted such that the incident angle to the sensing surface 110 of the irradiation light from the light source 10 and the reflection angle therefrom are 47° so as to satisfy the condition.

Next, the light source 20 for scattering will be described. The light source 20 for scattering also can irradiate directional irradiation light and is disposed at a position and an angle that allow the irradiated light to be incident at a predetermined angle with respect to the sensing surface 110. Herein, it is necessary to detect with high sensitivity the presence of a light scattered by the object in the light-receiving element portion 50, which is the light receiver, so that the configuration is such that the irradiation light of the light source 20 for scattering is not incident directly to the light-receiving element portion 50 when there is no object on the sensing surface. That is to say, the light source 20 for scattering is disposed at an angle displaced from the angle used for the light source 10 for total reflection so that the totally reflected light at the windshield of the light source for scattering is not incident directly on the light-receiving element portion 50. For example, the incident angle of the irradiation light of the light source 20 for scattering is set to an angle that does not satisfy Formula 1, which is the total reflection condition with respect to the sensing surface 110. In other words, when $n_1$ is the refractive index of outside material, $n_2$ is the refractive index of the windshield 100, and $\theta_1'$ is the angle at which the irradiation light is incident to the sensing surface, the angle $\theta_1'$ is set to be 41.47° or less, which is the condition that does not allow the light from the light source for scattering to be reflected totally. In the example of FIG. 1, $\theta_1'$ is 0°.

The prism 30a is a prism serving as a medium that brings the light source 10 for total reflection and the windshield 100 optically in contact with each other, and functions to guide the irradiated light from the light source 10 for total reflection into the windshield 100.

Even if there is no prism serving as a medium that brings the light source 20 for scattering and the windshield 100 optically in contact with each other, light for scattering can be let in, so that this prism is not necessarily provided, but can be provided.

The prism 30c functions to guide the reflected light from the light source 10 for total reflection on the sensing surface 110 and the scattered light from the light source 20 for scattering out from the windshield 100.

The condenser lens 40 is a lens for focusing light input from the prism 30c on the light-receiving element portion 50, which is the light receiver. The present invention is not limited thereto, and a configuration without a lens can be used.

The light-receiving element portion 50, which is the light receiver, is provided with a light-receiving element for outputting a photo detection signal in accordance with the amount of light irradiated, and the angle and the distance of the condenser lens 40 and the light-receiving element of the light-receiving element portion 50 are adjusted such that light incident on the condenser lens 40 is focused on the light-receiving element of the light-receiving element portion 50.

As described above, the light source 10 for total reflection, the prisms 30a and 30c, the condenser lens 40, and the light-receiving element portion 50 constitute an object sensor. The light source 20 for scattering, the prism 30c, the condenser lens 40, and the light-receiving element portion 50 constitute a light-scattering-object sensor. In the object-sensing device of Embodiment 1, the object detection mode in which the object sensor operates and the light scattering object detection mode in which the light-scattering-object sensor operates can be switched by switching the timing of the light irradiation by the light source 10 for total reflection and the timing of the light irradiation by the light source 20 for scattering. Although a control portion is not shown in FIG. 1, it is assumed that there is a control portion provided with functions for controlling the light source 10 for total reflection to be on/off, controlling the light source 20 for scattering to be on/off, and notifying the object-estimating portion 60 of an operation mode, that is, whether or not the mode is the object detection mode or the light scattering object detection mode. The object-estimating portion 60 can serve also as the control portion.

Next, the object-estimating portion 60 will be described. The object-estimating portion 60 is a portion for receiving a photo detection signal from the light-receiving element portion 50 and analyzing the photo detection signal to estimate the presence of the object, the kind of the object, and the state of the object. Since estimation is performed by using a relative change from the previous photo detection signal value in each mode in the estimation process, the object-estimating portion 60 includes a latch portion for latching the photo detection signal value detected in the previous detection in each mode. The latch portion for a photo detection signal in the object detection mode is referred to as a first latch portion, and the latch portion for a photo detection signal in the light scattering object detection mode is referred to as a second latch portion.

Hereinafter, the process for estimating the presence of an object, the kind of the object, and the state of the object with the object-estimating portion 60 will be described. First, the concept of the estimation process with the object estimation portion 60 will be described with respect to an object when a rain drop is attached on the sensing surface 110 as the object.

Figure 2B:
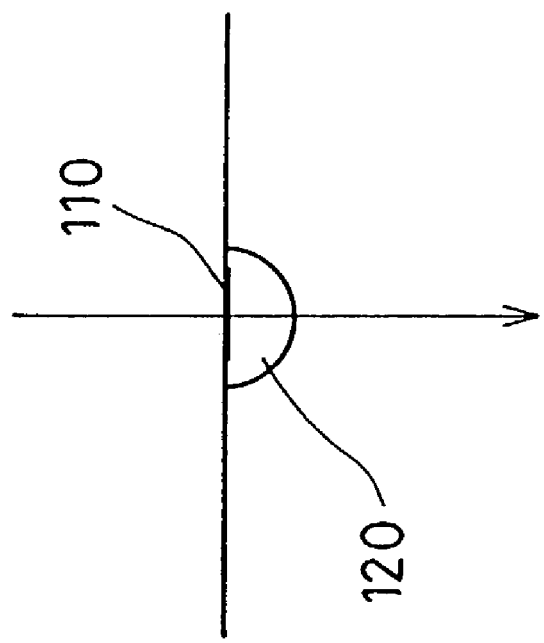
FIG. 2 is a view illustrating a concept of an estimation process with respect to an object by an object-estimating portion 60 when a rain drop is on a sensing surface 110.
Figure 2A:
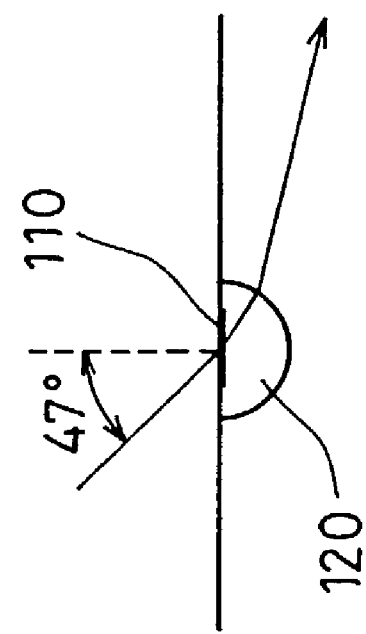

FIG. 2A is a schematic view showing the manner in which light is traveling in the object detection mode when a rain drop is on the sensing surface. In the object detection mode, light is irradiated from the light source 10 for total reflection onto the sensing surface 110, and the light source 20 for scattering is turned off in the object detection mode. Since the rain drop is present on the sensing surface 110, as discussed above, the total reflection condition on the sensing surface 110 is not satisfied, so that irradiated light escapes to the outside. In this case, no light is received by the light-receiving element portion 50. In principle, "signal level drop" with respect to the previous signal level is detected in the photo detection signal received by the object-estimating portion 60 in the object detection mode.

FIG. 4 is a diagram showing an example of photo detection signals detected by the light-receiving element portion 50. The horizontal axis is the time axis, and the modes are switched alternately. Reference numeral 401 denotes the object detection mode, 402 denotes the light scattering object detection mode, 403 denotes the object detection mode, and 404 denotes the light scattering object detection mode. In this manner, the modes alternate with each other.

Figure 4A:
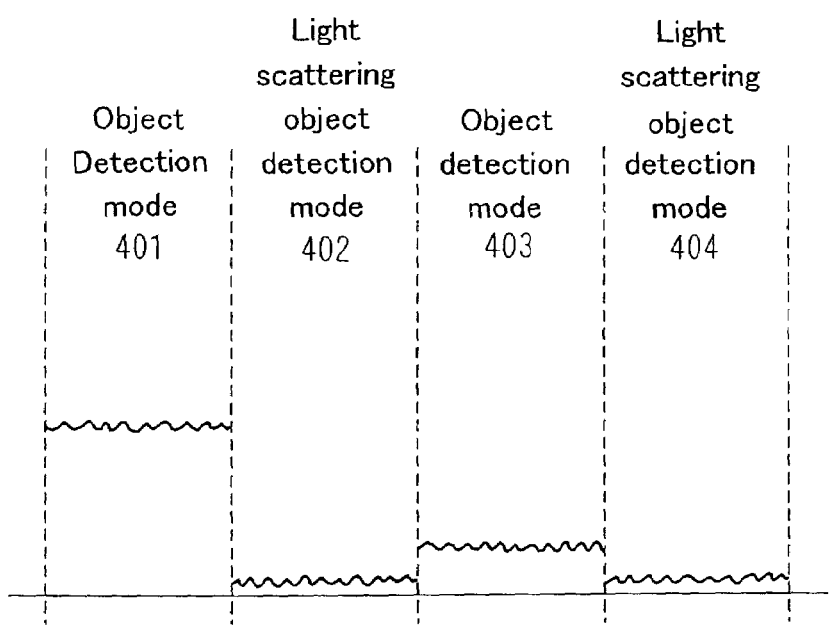
FIG. 4 is a diagram showing an example of photo detection signal levels obtained from a light-receiving element portion 50 of the first object-sensing device of the present invention.

FIG. 4A shows an example of a photo detection signal when the object is a rain drop. As shown in FIG. 4A, the object-estimating portion 60 detects that the signal level of the latest object detection mode 403 is lower than that of the previous object detection mode 401 that is latched in the first latch portion. The reference signal values are not necessarily managed with absolute values, and the device may start to operate from a default state and only a relative change from a signal value captured in the previous object detection mode may be used for determination. However, it is preferable to set a threshold value in a ratio in relative changes and determine that "the signal level is dropped", only when the signal level is dropped more than the threshold value in order to eliminate the influence of noise.

FIG. 2B is a schematic view showing the manner in which light is traveling in the light scattering object mode when a rain drop is attached on the sensing surface. In the light scattering detection mode, light is irradiated from the light source 20 for scattering onto the sensing surface 110, and the light source 10 for total reflection is turned off in the light scattering object detection mode. A rain drop is present on the sensing surface 110, but the light scattering properties of the rain drop are poor, so that light scattering does not occur in principle, and therefore the irradiated light escapes to the outside. In this case, the light-receiving element portion 50 receives no light. The photo detection signal received by the object-estimating portion 60 in the light scattering object detection mode is in a low level.

In the example of the photo detection signal of FIG. 4A, the signal level of the latest light scattering object detection mode 404 is at a low level similarly to the photo detection signal level of the previous light scattering object detection mode 402 that is latched in the second latch portion. However, it is preferable to set a certain threshold value and determine that "the signal level is low", only when the signal level does not exceed the threshold value in order to eliminate the influence of noise.

The object-estimating portion 60 estimates the presence of a rain drop, that is, the presence of an object having poor light scattering properties, when "signal level drop" is obtained in the object detection mode and "no change in the signal level (low level is maintained)" is obtained in the light scattering object detection mode. FIG. 8 is a diagram showing an estimation of the presence of the object, the kind of the object and the state of the object with the photo detection signal level in the object detection mode and the light scattering detection mode, and the above estimation of the rain drop corresponds to the case of (2) of FIG. 8.

Next is described the concept of an estimation process with respect to an object by the object-estimating portion 60 when muddy water is attached on the sensing surface 110 as the object.

Figure 3B:
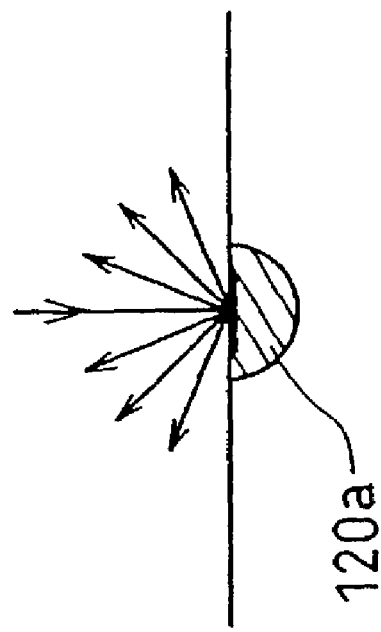
FIG. 3 is a view illustrating the concept of an estimation process with respect to an object by an object-estimating portion 60 when muddy water is on a sensing surface 110.
Figure 3A:
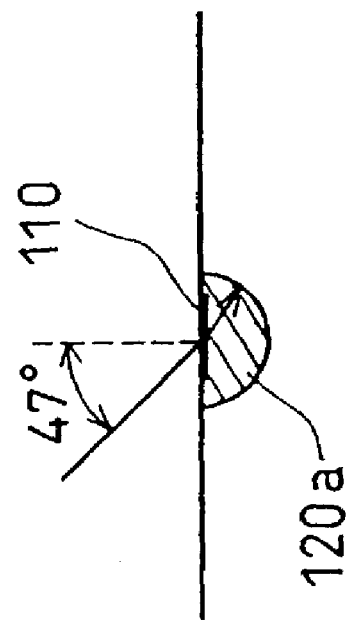

FIG. 3A is a schematic view showing the manner in which light is traveling in the object detection mode when muddy water is attached on the sensing surface. Similarly to the case of FIG. 2A, light is irradiated from the light source 10 for total reflection onto the sensing surface 110, and the light source 20 for scattering is turned off. Since the muddy water 120*a* is present on the sensing surface 110, the total reflection condition on the sensing surface 110 is not satisfied, so that irradiated light escapes to the outside, or is scattered or absorbed in the muddy water, and no light is received by the light-receiving element portion 50. The object-estimating portion 60 compares and analyzes a photo detection signal received in the object detection mode so that "signal level drop" with respect to the previous signal level can be detected.

Figure 4B:
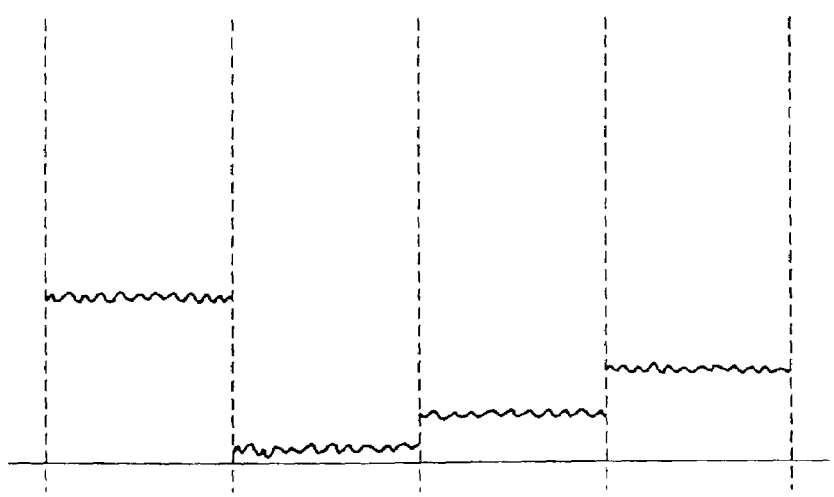

FIG. 4B shows an example of a photo detection signal when the object is muddy water. As in the case of FIG. 4A, the object-estimating portion 60 detects that the signal level of the latest object detection mode 403 is lower than that of the previous object detection mode 401 that is latched in the first latch portion.

FIG. 3B is a schematic view showing the manner in which light is traveling in the light scattering object mode when muddy water is on the sensing surface. Light is irradiated from the light source 20 for scattering onto the sensing surface 110, and the light source 10 for total reflection is turned off. Light from the light source for scattering falls on the object that is muddy water 120*a*. Since the muddy water 120*a* has light scattering properties, light scattering occurs. Therefore, scattered light is released from the muddy water 120*a* to the surroundings, and a part thereof is received by the light-receiving element portion 50 via the prism 30*c* and the condenser lens 40. The photo detection signal received by the object-estimating portion 60 in the light scattering object detection mode in principle means "a signal level increase" with respect to the previous signal level.

In the example of the photo detection signal of FIG. 4B, the signal level of the latest light scattering object detection mode 404 is higher than the signal level in the vicinity of the "0" level of the previous light scattering object detection mode 402 that is latched in the second latch portion. However, it is preferable to set a certain threshold value and determine that the signal level is increased only when the signal level exceeds the threshold value in order to eliminate the influence of noise.

The object-estimating portion 60 estimates the presence of muddy water, that is, the presence of an object having light scattering properties, when "signal level drop" is obtained in the object detection mode and "signal level increase" is obtained in the light scattering object detection mode. This estimation corresponds to the case of (3) of FIG. 8. The process for estimating the state in which the muddy water has a water content or the state in which the mud is dry in distinction from each other will be described later in Embodiment 2.

The object-estimating portion 60 estimates that the object has been removed from the sensing surface when "signal level increase" is detected in the object detection mode, and estimates that the light scattering object has been removed from the sensing surface when "signal level drop" is detected in the light scattering detection mode. This estimation corresponds to (5) of FIG. 8.

Figure 5:
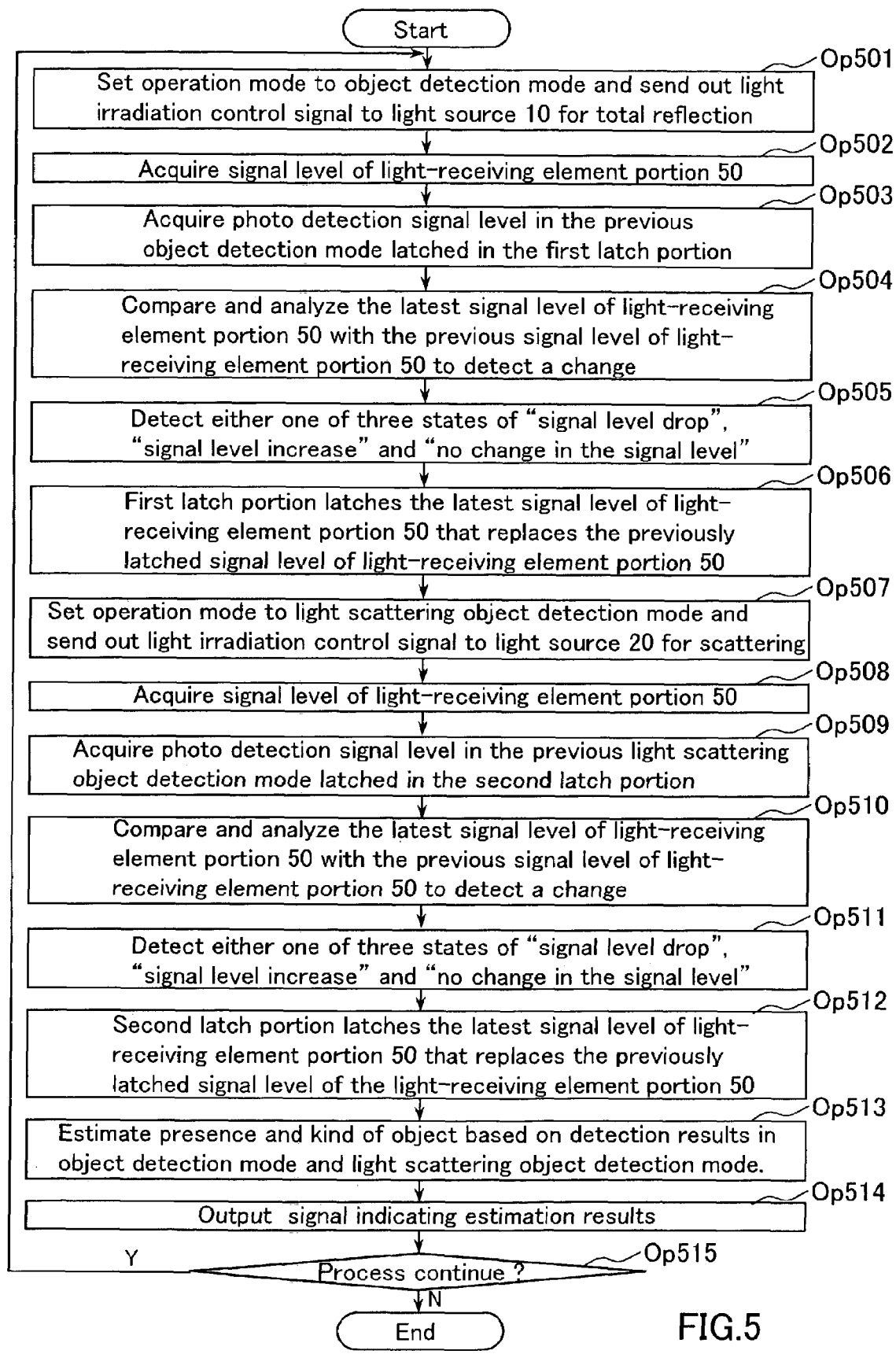
FIG. 5 is a flowchart showing a process for estimating the presence of an object, the kind of the object and the state of the object with the object-estimating portion 60 of the first object-sensing device of the present invention.

FIG. 5 is a flowchart showing a process for estimating the presence of an object, the kind of the object and the state of the object by the object-estimating portion 60 of the object-sensing device of Embodiment 1. In this example, the object-estimating portion 60 serves also as a control portion for switching the object detection mode and the light scattering object detection mode, and is provided with a latch function to latch a photo detection signal value.

First, the object-estimating portion 60 sets the operation mode to the object detection mode and sends out a light irradiation control signal to the light source 10 for total reflection (operation Op 501). The light source 10 for total reflection irradiates irradiation light onto the sensing surface 110, and the light-receiving element portion 50, which is a light receiver, receives reflected light from the sensing surface 110.

Next, the object-estimating portion 60 acquires the signal level of the light-receiving element portion 50 (operation Op 502). This latest signal level is a signal based on which the presence of an object is estimated.

Next, the object-estimating portion 60 acquires the photo detection signal level detected from the light-receiving element portion 50 in the previous object detection mode that is latched in the first latch portion (operation Op 503). In a process in an initial state in which there is no previously latched signal, the signal level of an initial value is set to "low level".

Next, the object-estimating portion 60 compares and analyzes the latest signal level of the light-receiving element portion 50 with the previous signal level of the light-receiving element portion 50 to detect a change (operation Op 504).

The object-estimating portion 60 has a threshold value to determine whether the relative change ratio of the two signal levels is "signal level drop" or "signal level increase", and detects either one of three states of "signal level drop", "signal level increase" and "no change in the signal level" (operation Op 505).

Next, the first latch portion of the object-estimating portion 60 latches the latest signal level of the light-receiving element portion 50 that replaces the previously latched signal level of the light-receiving element portion 50 (operation Op 506).

Next, the object-estimating portion 60 sets the operation mode to the light scattering object detection mode and sends out a light irradiation control signal to the light source 20 for scattering (step 507). The light source 20 for scattering irradiates irradiation light onto the sensing surface 110, and the light-receiving element portion 50, which is a light receiver, receives scattered light from the sensing surface 110.

Next, the object-estimating portion 60 acquires the signal level of the light-receiving element portion 50 (operation Op 508). This latest signal level is a signal based on which the presence of a light scattering object is estimated.

Next, the object-estimating portion 60 acquires the photo detection signal level detected from the light-receiving element portion 50 in the previous light scattering object detection mode that is latched in the second latch portion (operation Op 509). In a process in an initial state in which there is no previously latched signal, the signal level of an initial value is set to "low level".

Next, the object-estimating portion 60 compares and analyzes the latest signal level of the light-receiving element portion 50 with the previous signal level of the light-receiving element portion 50 to detect a change (operation Op 510).

The object-estimating portion 60 has a threshold value to determine whether the relative change ratio of the two signal levels is "signal level drop" or "signal level increase", and detects either one of three states of "signal level drop", "signal level increase" and "no change in the signal level" (operation Op 511).

Next, the second latch portion of the object-estimating portion 60 latches the latest signal level of the light-receiving element portion 50 that replaces the previously latched signal level of the light-receiving element portion 50 (operation Op 512).

Next, the object-estimating portion 60 estimates the presence of an object and the kind of the object based on the table shown in FIG. 8, in accordance with a combination of either one of the three states of "signal level drop", "signal level increase" and "no change in the signal level" detected in the object detection mode in operation Op 505 and either one of the three states of "signal level drop", "signal level increase" and "no change in the signal level" detected in the light scattering object detection mode in operation Op 511 (operation Op 513).

According to the above configuration, the four states of "no object", "rain drops (object having light transmission properties)", "muddy water (object having light scattering properties)", and "object removed" as shown in (1), (2), (3), and (5) of FIG. 8 can be estimated.

The object-estimating portion 60 outputs an output signal indicating the above-described estimation results (operation Op 514), goes back to operation Op 501 when the process continues (operation Op 515: Y), and ends the process when the process does not continue (operation Op 515: N).

In the above description, the object detection mode comes first, and the light scattering object detection mode comes after that, but the order can be opposite.

As described above, the object-sensing device of Embodiment 1 makes it possible to estimate whether or not an object is present on the sensing surface and whether or not the object is a substance having light scattering properties, and in particular, to distinguish whether the object is a rain drop, muddy water or other substances as shown as examples.

(Embodiment 2)

An object-sensing device of Embodiment 2 is an example in which an additional application function is provided for the process for estimating the kind and the state of an object in the object-sensing device of Embodiment 1 of the present invention. In particular, in this embodiment, it is estimated whether muddy water is in the state of so-called "muddy water" having a water content or in a dry state in distinction from each other when the object is muddy water, for example.

The device configuration and the arrangement of the components can be the same as in Embodiment 1, so that the description thereof is omitted. The process of the object-estimating portion 60 is different.

First, the principle of estimating whether muddy water is in the state of so-called "muddy water" having a water content or it is dry mud in distinction from each other will be described.

The so-called "muddy water" having a water content will not be described in detail, because it is described in Embodiment 1. The path of light in the object detection mode is the same as in FIG. 3A. The signal level can be detected in the same manner as in FIG. 4A, and "signal level drop" relative to the previous signal level is detected. In the light scattering object detection mode, as shown in FIG. 3B, the presence of muddy water on the sensing surface 110 causes scattering on the sensing surface 110, and a part of the scattered light is captured by the light-receiving element portion 50, which is a light receiver. Thus, "signal level drop" relative to the previous signal level is detected, as shown in FIG. 4B.

Figure 6A:
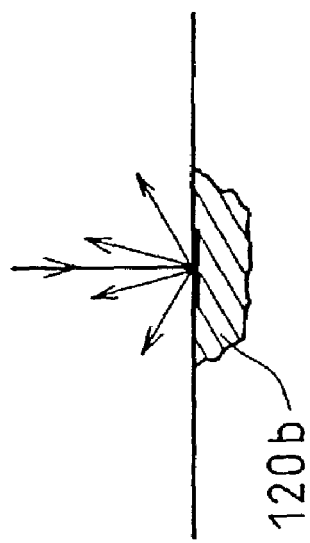
FIG. 6 is a view illustrating the concept of an estimation process with respect to an object by the object-estimating portion 60 when the object in the state of dry muddy water is on a sensing surface 110.

Then, FIG. 6A is a schematic view showing the manner in the object detection mode when dry mud is attached on the sensing surface 110. In the object detection mode, as in the case of muddy water having a water content in FIG. 3A, the presence of dry muddy water on the sensing surface 110 causes a part of irradiation light to be scattered or absorbed in the mud, so that the light becomes relatively smaller than when totally reflected light is received. However, the scattered light of a part of the irradiation light is received by the light-receiving element portion 50. Therefore, a drop in the photo detection signal level is relatively smaller than in the case of a rain drop. Thus, the object-estimating portion 60 detects "signal level drop" relative to the previous signal level.

Figure 6B:
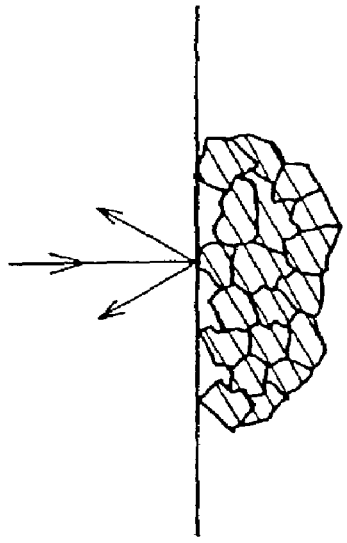
Figure 6C:
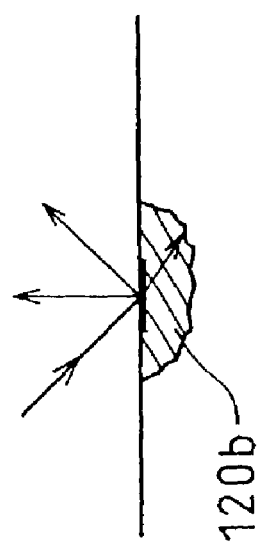
Figure 6D:
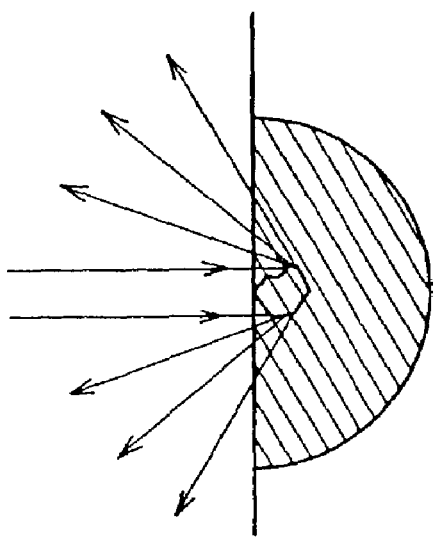

Then, FIG. 6B is a schematic view showing the manner in the light scattering object detection mode when dry mud is attached on the sensing surface 110. In the light scattering object detection mode, as in the case of muddy water having a water content in FIG. 3B, the presence of dry mud 120b on the sensing surface 110 causes light scattering on the sensing surface 110, and a part of the scattered light is received by the light-receiving element portion 50, but the amount of the light received by the light-receiving element portion 50 becomes relatively smaller than in the case of light scattering by the muddy water having a water content. The light scattering photo detection level becomes relatively smaller than in the case of the muddy water having a water content for the following reason. In the case of muddy water having a water content, as shown in FIG. 6(C), the presence of the water content allows close contact with the sensing surface 110, and light scattering occurs in the entire area that is in contact with the muddy water. On the other hand, dry mud is not in close contact with the sensing surface 110 because of no water content, as shown in FIG. 6(D), so that light scattering occurs only at the contact points of mud particles with respect to the sensing surface.

In principle, the object-sensing device of Embodiment 2 analyzes the photo detection signal level of the light-receiving element portion 50 in the light scattering object detection mode so as to estimate whether the water content of the object is excessive, that is, the object is muddy water with a water content or dry muddy water in distinction from each other. An example of a process for estimating whether or not the object has an excessive water content is to compare the latest signal level of the light-receiving element portion 50 with the previous signal level of the light-receiving element portion 50 in the light scattering object detection mode and estimate whether or not the water content of the object is excessive based on the excessiveness of the ratio of "signal level increase" thereof. In some cases, it is difficult to obtain the ratio of the signal level increase, for example, because the previous signal level of the light-receiving element portion 50 is as small as in the vicinity of "0 level". In that case, it is possible to estimate whether or not the water content of the object is excessive based on the excessiveness of the absolute value of the signal level, and also possible to determine it, based on both the relative change and the absolute change.

Thus, the estimating portion 60 estimates that muddy water with a water content is attached, when it is determined to be "signal level drop" in the object sensor operation mode and it is determined to be "signal level increase (large increase ratio)" in the light-scattering-object sensor operation mode. The estimating portion 60 estimates that dry mud is attached, when it is determined to be "signal level drop" in the object sensor operation mode and it is determined to be "signal level increase (small increase ratio)" in the light-scattering-object sensor operation mode. The degree of dryness can be estimated in view of the magnitude of the signal level change.

Figure 7:
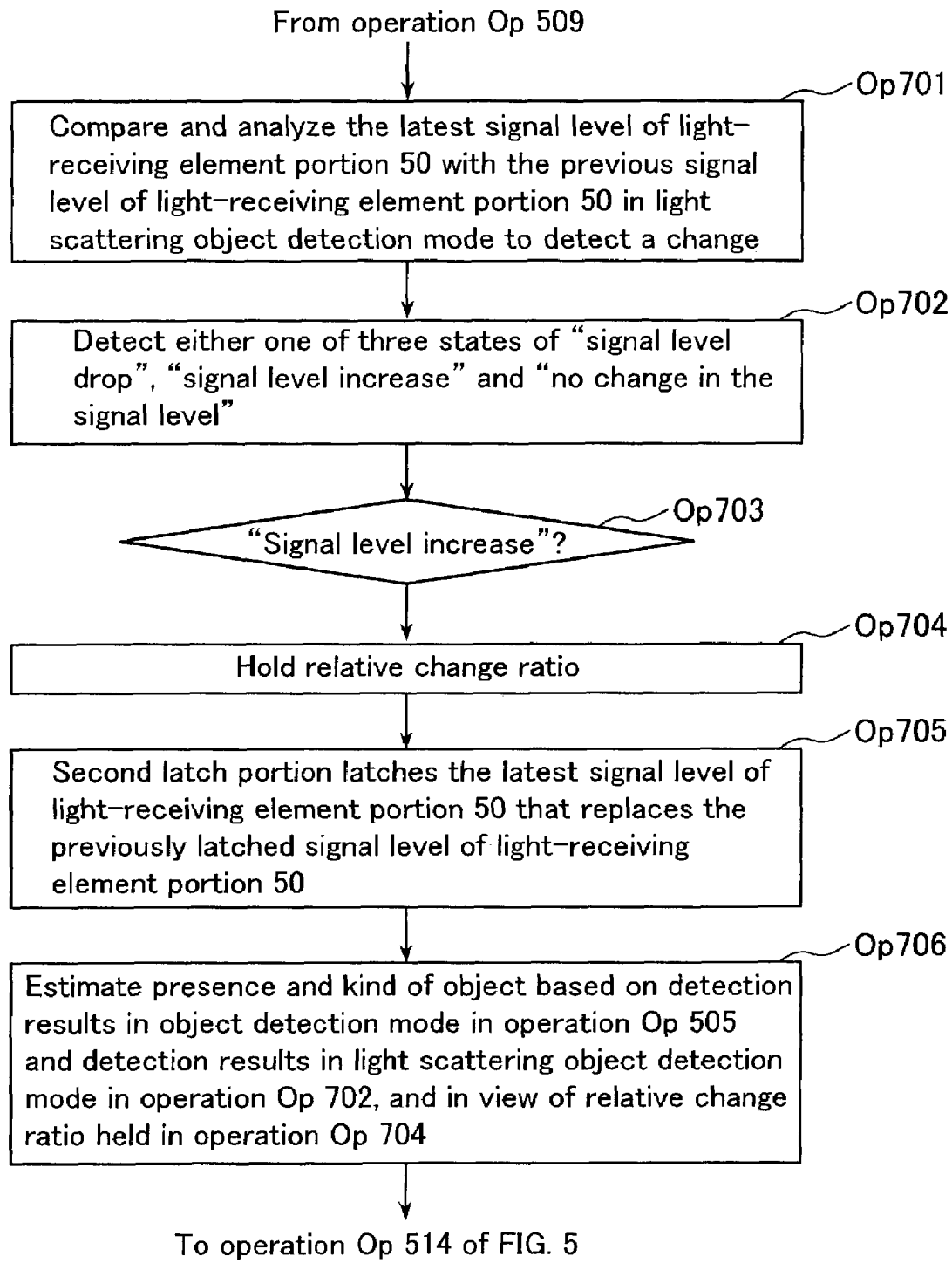
FIG. 7 is a flowchart showing a process for estimating the presence of an object, the kind of the object and the state of the object with an object-estimating portion 60 of a second object-sensing device of the present invention according to Embodiment 2.

FIG. 7 is a flowchart showing a process for estimating the presence of an object, the kind of the object and the state of the object by the object-estimating portion 60 of the object-sensing device of Embodiment 2. In this example, the object-estimating portion 60 serves also as a control portion for switching the object detection mode and the light scattering object detection mode, and is provided with a latch function to latch a photo detection signal value.

In the estimation process step by the object-estimating portion 60 of the object-sensing device of the present invention, the steps after the start can be the same as the operations Op 501 to Op 506 in the object detection mode up to the operations Op 507 to Op 509 after moving onto the light scattering object detection mode, as shown in FIG. 5 of Embodiment 1, so that these steps are not shown in the flowchart of FIG. 7.

In the operation Op 509, the object-estimating portion 60 acquires the photo detection signal level detected from the light-receiving element portion 50 in the previous light scattering object detection mode that is latched in the second latch portion, and then compares and analyzes the latest signal level of the light-receiving element portion 50 with the previous signal level of the light-receiving element portion 50 to detect a change (operation Op 701).

The object-estimating portion 60 has a threshold value to determine whether the relative change ratio of the two signal levels is "signal level drop" or "signal level increase", and detects either one of three states of "signal level drop", "signal level increase" and "no change in the signal level" (operation Op 702).

In the case of "signal level increase" (operation Op 703: Y), the object-estimating portion 60 holds the relative change ratio (operation Op 704).

Next, the second latch portion of the object-estimating portion 60 latches the latest signal level of the light-receiving element portion 50 that replaces the previously latched signal level of the light-receiving element portion 50 (operation Op 705).

Next, the object-estimating portion 60 estimates the presence of an object and the kind of the object based on the table shown in FIG. 8, in accordance with a combination of either one of the three states of "signal level drop", "signal level increase" and "no change in the signal level" detected in the object detection mode in operation Op 505 and either one of the three states of "signal level drop", "signal level increase" and "no change in the signal level" detected in the light scattering object detection mode in operation Op 702, and further in view of the relative change ratio in the case of "signal level increase" held in operation Op 704 (operation Op 706). In this operation Op 706, it is possible to estimate with the absolute value of the signal level of the light-receiving element portion 50 in the light scattering object detection mode that is latched in the second latch portion in the operation Op 705. As shown in (3) and (4) of FIG. 8, in the estimation that the object is muddy water, when the relative change ratio of "signal level increase" is large, it is estimated to be "muddy water having a water content". When the relative change ratio of "signal level increase" is small, it is estimated to be "dry muddy".

The output of the estimation results, the process continuation confirmation and the end process can be the same as those in Embodiment 1, and after the operation Op 706, the process goes to the operation Op 514 of FIG. 5.

In the above description, the object detection mode comes first, and the light scattering object detection mode comes after that, but the order can be opposite.

The object-sensing device of Embodiment 2 makes it possible to estimate the kind of the object and the excessiveness of the water content of the object in the process for estimating the kind of the object and the state thereof. When the object is muddy water, a distinction as to whether the muddy water is in the state of so-called "muddy water" or dry mud can be performed in the estimation.

(Embodiment 3)

An embodiment of a second object-sensing device of the present invention will be described.

The second object-sensing device of Embodiment 3 includes a light-receiving element array corresponding to the sensing surface, and light obtained via the sensing surface forms an image in the light-receiving element array by an imaging system lens and thus is received, and photo detection signals are formed into a signal pattern corresponding to an alignment of micro-light-receiving elements. The change portion of the signal pattern is analyzed, so that the presence of an object on the sensing surface, the kind thereof, or the like is detected. First, as Embodiment 3, an object-sensing device that can estimate the presence of an object on the sensing surface and whether or not the object is a substance having light scattering properties will be described. In particular, by taking as an example the case where the object is a rain drop and the case where the object is muddy water, it is shown that the two cases can be distinguished.

The second object-sensing device of the present invention has a configuration, for example, like the first object-sensing device, where the object detection mode using the light source of total reflection and the light scattering object detection mode using the light source for scattering are provided in order to estimate the presence, the kind and the state of the object on the sensing surface of a transparent substrate. Alternatively, a configuration without the object detection mode and only with the light scattering object detection mode, or a configuration without the light scattering object detection mode and only with the object detection mode can be configured as alternative embodiments. The basic principle of the object-sensing device of the present invention is as follows. A reflected light from the light source for total reflection and scattered light of the light source for scattering that are irradiated onto a sensing surface are received by a light receiver, and the photo detection signals are formed into a signal pattern and analyzed so that a change in the total reflection condition and the scattering condition on the sensing surface due to the presence, the kind and the state of the object on the sensing surface is detected, so that the presence, the kind and the state of the object are estimated.

Figure 9A:
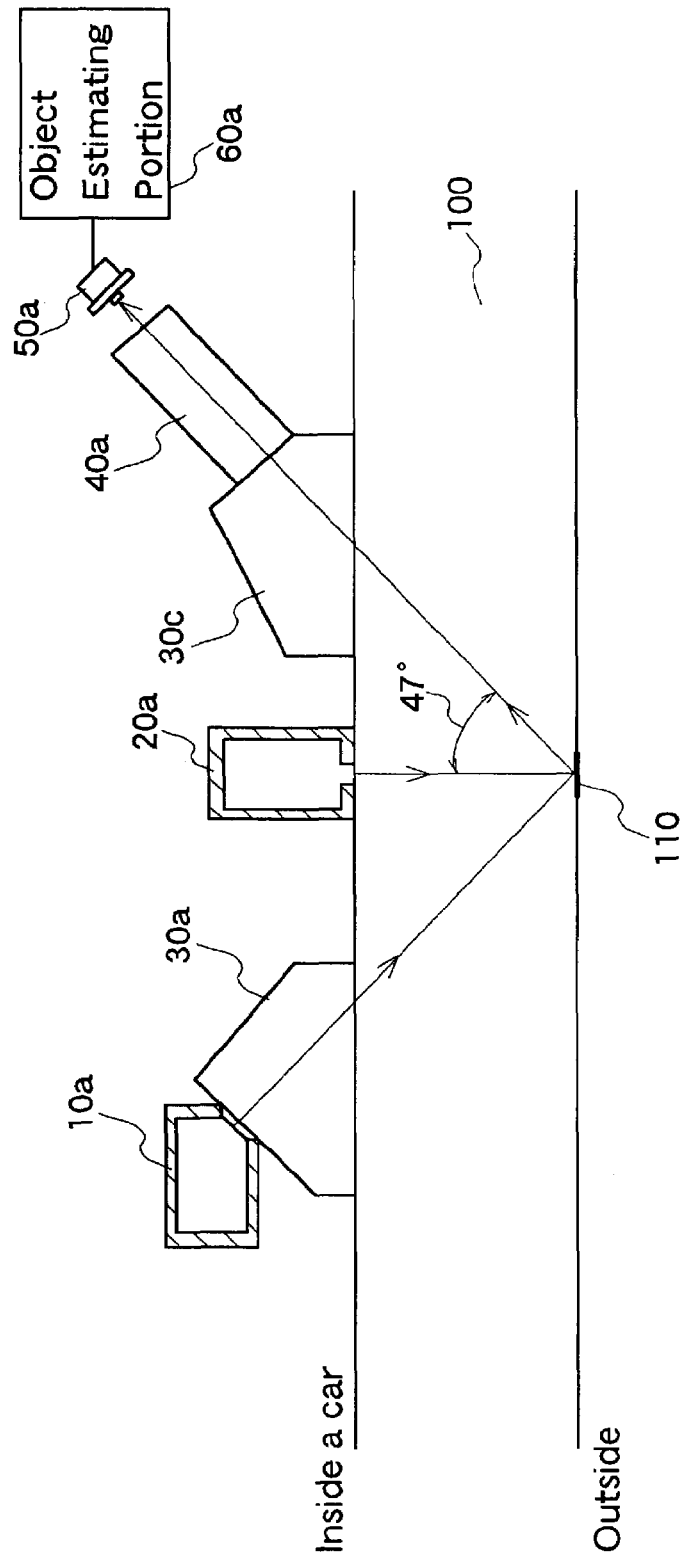
FIG. 9 is a schematic view simply showing an example of a device configuration of the second object-sensing device of the present invention.
Figure 9C:
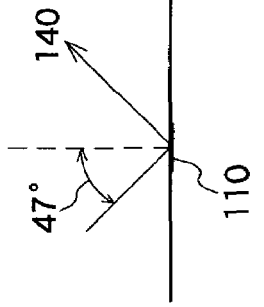
Figure 9B:

A device configuration example of the object-sensing device of the present invention will be described. FIG. 9 is a simplified schematic view showing an example of a device configuration of the object-sensing device of the present invention of Embodiment 3. This shows the cross-section of the device configuration, and a plurality of each component in the cross-section is arranged in an array in the direction perpendicular to the paper sheet of the drawing. In FIG. 9, reference numeral 100 denotes a windshield 100 as an example of a transparent substrate. The layer below the windshield 100 is the outside. A sensing surface 110 is in a predetermined region in on a boundary surface between the windshield 100 and the outside. Reference numeral 10a denotes a light source for total reflection, and reference numeral 20a denotes a light source for scattering. Reference numerals 30a and 30c are prisms. Reference numeral 40a denotes an imaging lens, and reference numeral 50a denotes a light-receiving element portion (charge coupled device) as a light receiver. Reference numeral 60a denotes an object-estimating portion. In this example, the light source 10a for total reflection, the prisms 30a and 30c, the imaging lens 40a, and the light-receiving element portion 50a constitute an object sensor. The light source 20a for scattering, the prism 30c, the imaging lens 40a, and the light-receiving element portion 50a constitute a light-scattering-object sensor.

The light source 10a for total reflection has a plurality of light sources such as LED at one end or both ends, and light beams are emitted from an linear opening portion. The angle at which the light source 10a for total reflection is provided is the same as in Embodiment 1, and the light incident angle $\theta_1$ is selected from the range of $41.47° < \theta_1 < 61.74°$. Also in the example of this embodiment, the arrangement is adjusted such that the incident angle and the reflection angle of the irradiation light from the light source 41a for total reflection onto the sensing surface 110 are 47°.

Next, the light source 20a for scattering will be described. Like the light source 10a for total reflection, the light source 20a for scattering also has a plurality of light sources such as LEDs at one end or both ends, and beams are emitted from a linear opening portion. The angle at which the light source 20a for scattering is provided is the same as in Embodiment 1, and the light incident angle $\theta_1'$ of the irradiation light of the light source 20a for scattering is $41.47° < \theta_1$, which are angles that does not allow the total reflection condition to be satisfied with respect to the sensing surface 110. In this example, $\theta_1'$ is set to 0°.

Figure 10A:
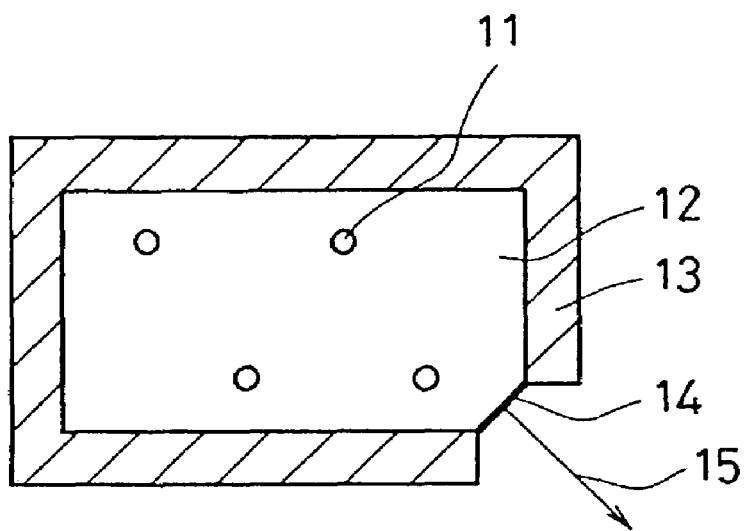
FIG. 10A is a schematic view showing the end face of a light source portion 10a of the second object-sensing device of the present invention.
Figure 10B:
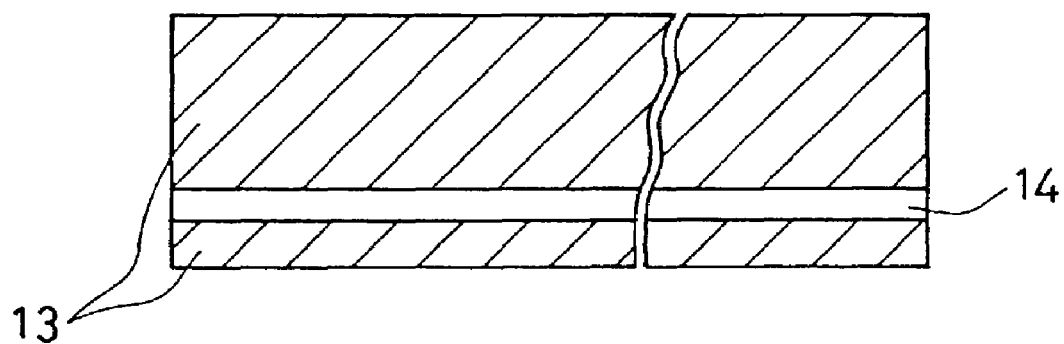
FIG. 10B is a view of the light source portion 10 viewed from the front in which an opening portion 14 can be seen.

FIG. 10A shows an end face of the light source 10 for total reflection, and FIG. 10B is a view showing the front face in which an opening portion 14 is seen. The light source 10a for total reflection includes, for example, a plurality of light sources provided at end portions, and light is emitted from the linear opening portion 14. Beams are emitted from the linear opening portion 14, and a plurality of beams is let out as straight light 15 traveling in parallel. In FIG. 10A, reference numeral 11 denotes a LED as a light source, reference numeral 12 is a conductor made of a transparent material, reference numeral 13 denotes a cover for shielding light, reference numeral 14 is an opening portion from which LED light is emitted, and reference numeral 15 denotes a beam emitted from the LED. The LED 11 is provided at the left or right end or both ends in FIG. 10B, and reflection is repeated at the inner surface of the cover 13, leading to each portion of the opening portion 14. The LEDs can be arranged at the surface opposing the opening portion 14 of the conductor at an equal interval.

The light emitted from the opening portion 14 of FIG. 10B is incident on the prism 30a.

The size of a rain drop on the windshield 100 was examined. The size of an attached rain drop varies depending on the size of fallen rain drop and the state of object on the windshield 100, but examination is performed with specific values as general standards. In general, the diameter of a rain drop that is called misty rain is about 0.1 to 0.2 mm in the air. The diameter of a rain drop that is called a small rain drop is about 0.2 to 1 mm in the air. The diameter of a rain drop that is called a large rain drop is about 2 to 4 mm in the air. The diameter of a rain drop that is a particularly fierce rain drop such as an evening shower is about 4 to 6 mm in the air. The size of these rain drops attached on the windshield 100 varies depending on whether the glass surface is hydrophilic or water-repelling. It is assumed that the glass surface is water-repelling, and rain drops are attached on the surface with substantially the same size as that in the air. When a small rain drop having an average size, for example, a diameter of 0.5 mm is selected as the smallest rain drop to be detected, the area of the micro-region corresponding to one rain drop is about 0.2 mm². When a small rain drop having the smallest size, for example, a diameter of 0.2 mm is selected as the smallest rain drop to be detected, the area of the micro-region corresponding to one rain drop is about 0.03 mm$^2$.

Next, each prism will be described.

The prism 30a is a prism serving as a medium that brings the light source 10a for total reflection and the windshield 100 optically in contact with each other, and functions to guide the irradiated light from the light source 10a for total reflection into the windshield 100.

The prism 30c functions to guide the reflected light from the light source 10a for total reflection and the scattered light from the light source 20a for scattering on the sensing surface 110 out from the windshield 100.

Next, the imaging lens 40a will be described. The imaging lens 40a is configured so as to form an image formed on the sensing surface irradiated with irradiation light of the light source 10a for total reflection and the light source 20a for scattering on a micro-light-receiving element of the light-receiving element portion 50a. The angle and the distance of imaging lens 40a and the light-receiving element of the light-receiving element portion 50a are adjusted such that the image is formed on the light-receiving element of the light-receiving element portion 50a with the light incident to the imaging lens 40a.

Figure 11:
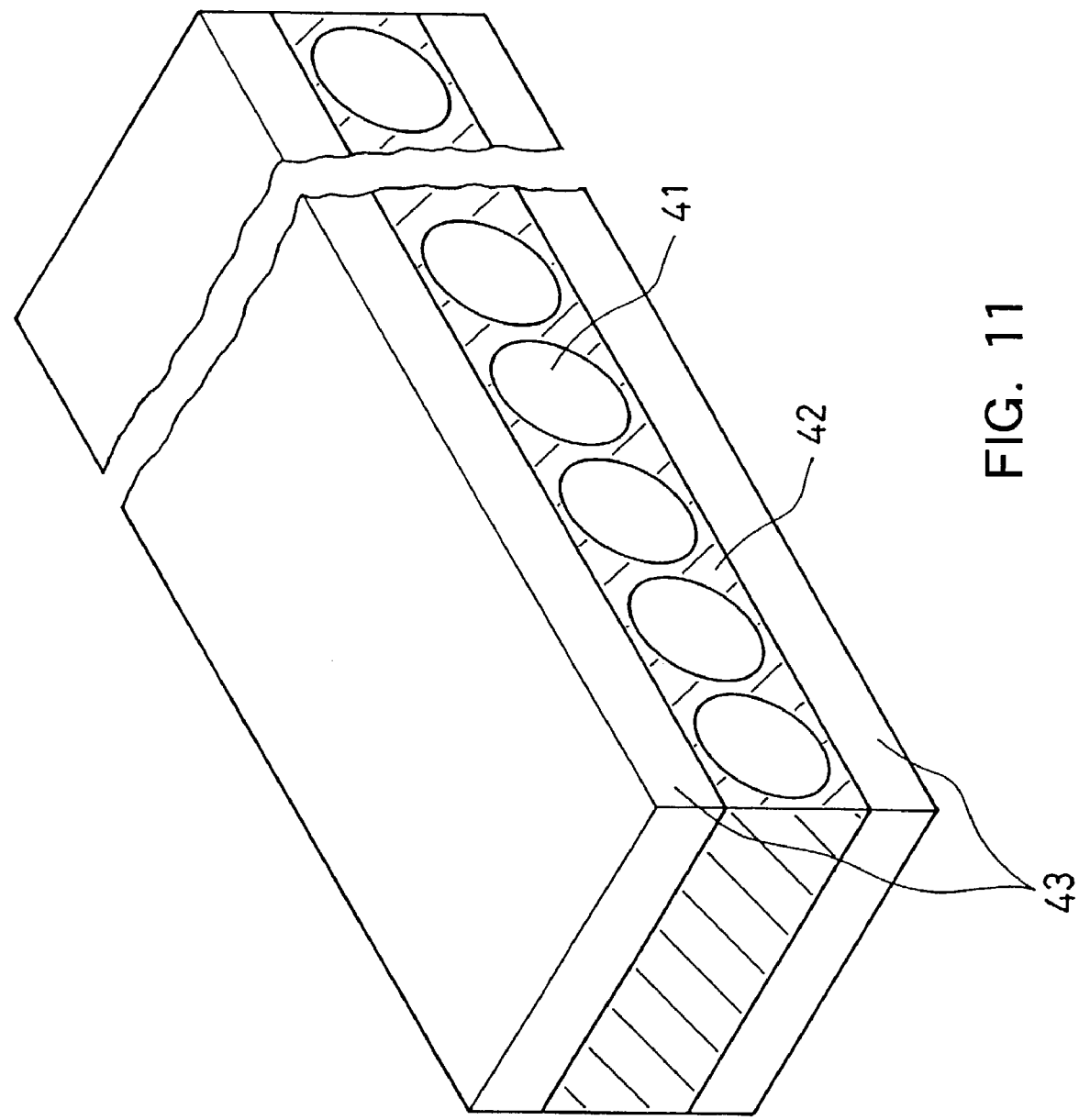
FIG. 11 is a schematic view showing an example of an imaging lens 40a of the second object-sensing device of the present invention.

FIG. 11 is a schematic view showing an example of the imaging lens 40a. Here, an example employing a refractive index distribution type lens array as the imaging lens 40a will be described. FIG. 11 is a view showing a basic configuration of SLA® (Selfoc Lense Array), which is one type of the refractive index distribution type lens array of an equal magnification imaging system. Reference numeral 41 is a rod lens as a small lens, reference numeral 42 is black resin, and reference numeral 43 is a FRP plate. The rod lens 41 is rod-shaped, and the lens face thereof is seen in FIG. 11. In the configuration view of FIG. 9, only one rod lens 41 is shown in cross-section. If this SLA is used, the incident beams are bent so as to form an erect image having an equal magnification at a predetermined position. In other words, an image can be formed on the light-receiving element array with the reflected light obtained from the sensing surface 110 as it is.

In the above example, the rod lenses 41 are arranged linearly, but the lenses can be arranged in accordance with the alignment of beams emitted from the light source 10a for total reflection and light source 20a for scattering and the arrangement of each light-receiving element of the light-receiving element portion 50a, which will be described later.

An example of an equal magnification imaging system has been described above, but it is important that the light-receiving surface of each light-receiving element, which is a light-receiving element of the light-receiving element portion 50a, and the sensing surface 110 forms an imaging optical system.

Next, the light-receiving element portion 50a, which is a light receiver, will be described.

The light-receiving element portion 50a has a plurality of micro-light-receiving elements, and the plurality of micro-light-receiving elements are arranged so as to correspond to parallel light of the light source 10a for total reflection or the light source 20a for scattering. In other words, the light-receiving element portion is provided with a micro light receiver for individually detecting the plurality of straight light irradiated from the light source 10a for total reflection or the light source 20a for scattering.

Figure 12:
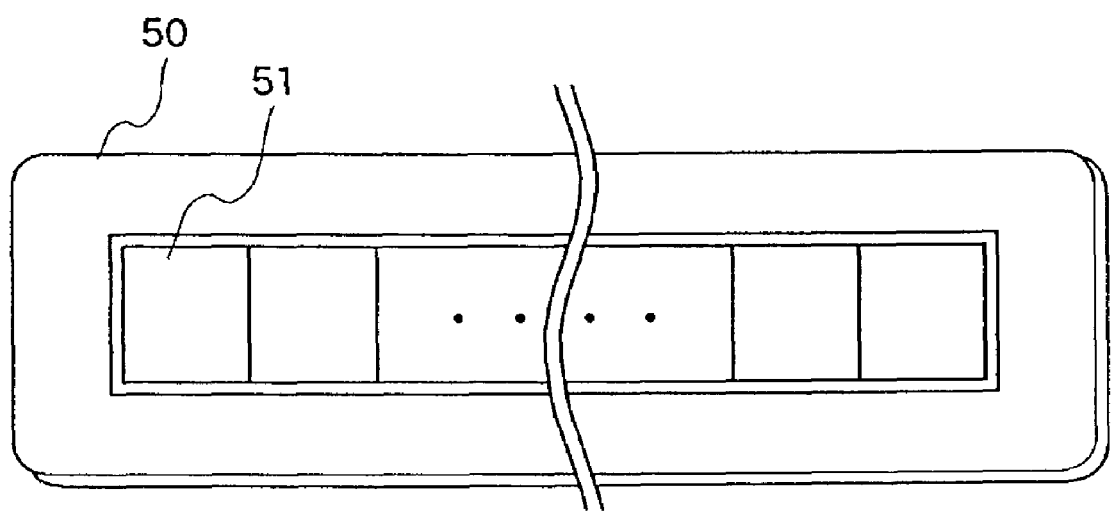
FIG. 12 is a schematic view showing an example of a light-receiving element portion 50a of the second object-sensing device of the present invention.

FIG. 12 is a schematic view showing an example of the light-receiving element portion 50a. In the example of FIG. 12, the light-receiving elements of the light-receiving element portion 50a are arranged linearly. Reference numeral 51 is each light-receiving element, that is, a conceptually shown light-receiving surface. Capacitors, transistor circuits, sense amplifier circuits and the like inside the light-receiving element 51 are not shown to clearly show a linear arrangement of the light-receiving surfaces of the light-receiving elements 51. The light-receiving surfaces of the light-receiving elements 51 are arranged so as to correspond to the arrangement of the opening portion 14 of the light source 10a for total reflection and the light source 20a for scattering, and the distance and the angle thereof are adjusted such that an image is formed with the reflected light from the sensing surface 110 via the imaging lens 40a.

The effective area of the light-receiving surface of the light-receiving element 51 can be adjusted corresponding to the area of an object to be detected. According to the examination of the size of an object to be detected on the sensing surface sensing surface 110, if the imaging lens 40a is of an equal magnification imaging system, the area preferably is about 0.2 mm$^2$ or less, more preferably about 0.03 mm$^2$ or less. However, a light-receiving element having an effective area of the light-receiving surface that is different from the above range can be used.

With the above-described components, the light source 10a for total reflection, the prisms 30a and 30c, the imaging lens 40a, and the light-receiving element portion 50a constitute an object sensor. The light source 20a for scattering, the prism 30c, the imaging lens 40a, and the light-receiving element portion 50a constitute a light-scattering-object sensor. FIG. 9 is a cross-sectional view and a plurality of each component is arranged in an array in the direction perpendicular to the sheet of the drawing. In the object-sensing device of Embodiment 3, the object detection mode, the light scattering object detection mode, and an outside incident light amount increase detection mode can be switched by switching the timing of the light irradiation by the light source 10a for total reflection and the timing of the light irradiation by the light source 20a for scattering. Although a control portion is not shown in FIG. 9, there is a control portion provided with functions for controlling the light source 10a for total reflection to be on/off, controlling the light source 20a for scattering to be on/off, and notifying the object-estimating portion 60a of an operation mode, that is, whether or not the mode is the object detection mode, the light scattering object detection mode or the outside incident light amount increase detection mode. The object-estimating portion 60a can serve also as the control portion.

Next, the object-estimating portion 60a will be described.

The object-estimating portion 60a is a portion for receiving a photo detection signal from the light-receiving element portion 50a and analyzing the photo detection signal to estimate the presence of the object, the kind of the object, and the shape of the object. The light-receiving element used in the second object-sensing device has a micro array structure, so that the object-estimating portion 60 receives photo detection signals from the light-receiving elements 51 of the light-receiving element portion 50 and analyzes the photo detection signals, so as to join the signal levels of the photo detection signals detected by the light-receiving elements in one mode, in accordance with the arrangement of the micro array structure and thus a signal pattern is derived. If there is a difference in the total reflection condition or a difference in the scattering condition due to objects such as rain drops on the sensing surface 110, the photo detection signal level in the corresponding micro-light-receiving element is different from other micro-light-receiving elements, and a drop portion or an increase portion appears in the signal pattern. The present invention detects the presence of an object on the sensing surface and the kind thereof by analyzing the signal pattern in this manner.

Hereinafter, the signal pattern of the object detection mode and the signal pattern of the light scattering object detection mode, and the analysis using these signal patterns will be described in detail.

First, the detection of the presence of an object and the detection of the kind of the object in the operation in the object detection mode and the light scattering object detection mode in the case where three rain drops are present on the sensing surface 110 will be described.

First, the operation in the object detection mode will be described.

Figures 13A, 13B:
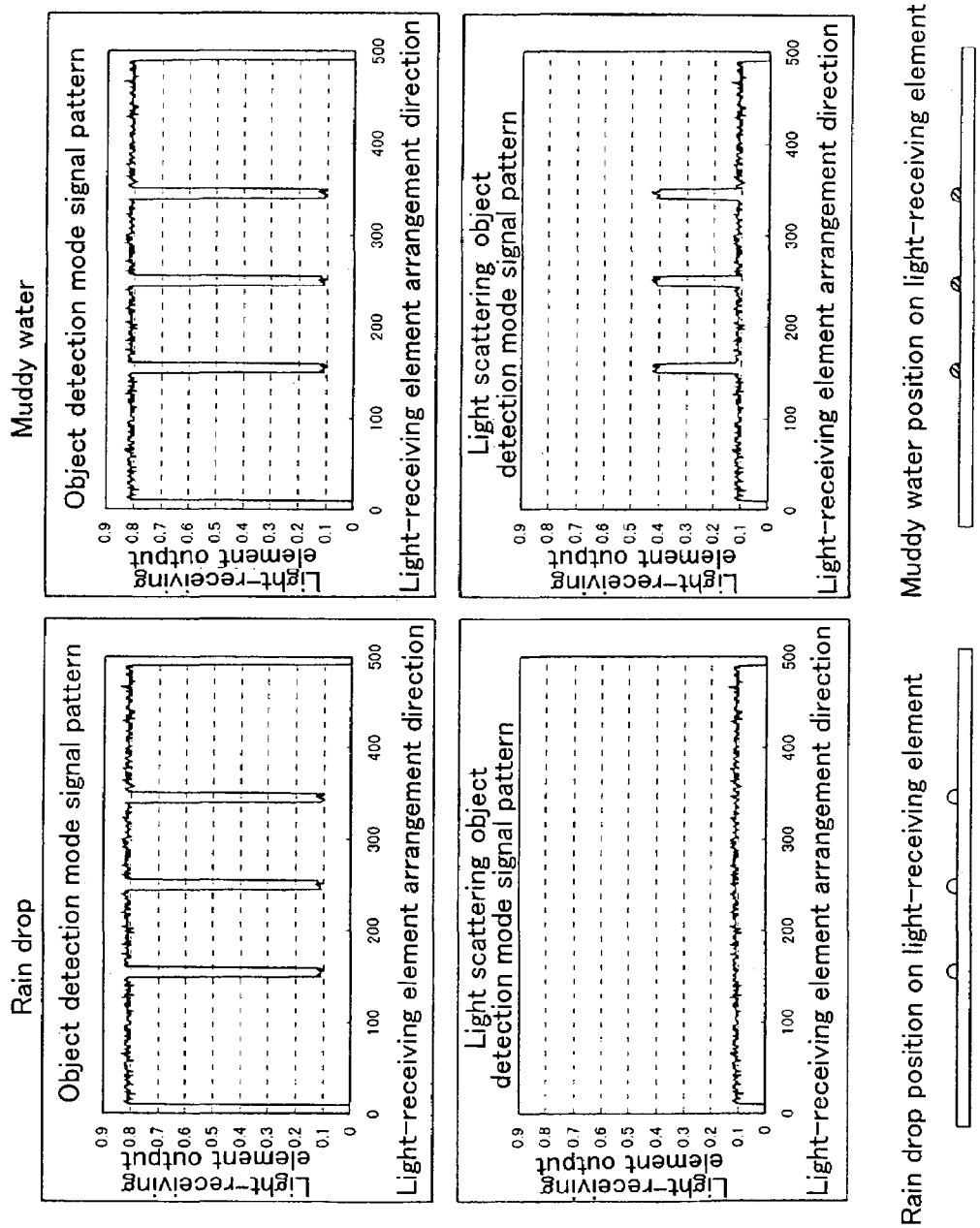
FIG. 13 is a signal pattern when the object detected by the second object-sensing device of the present invention is a rain drop and muddy water.

When rain drops are on the sensing surface 110, light travels in the object detection mode in the same manner as in FIG. 2A in Embodiment 1, in which the total reflection condition is not satisfied on the sensing surface 110, and irradiation light escapes to the outside. Therefore, in principle, light is not received by the corresponding light-receiving element of the light-receiving element portion 50a. Therefore, in the corresponding portion of the signal pattern, a drop portion of the signal level relative to the neighboring signal levels is detected. In this example, since there are three rain drops, three drop portions can be seen in the signal pattern. This case is shown in the upper signal pattern of FIG. 13A. As shown in the upper signal pattern of FIG. 13A, there are three pattern portions in which the signal level drops relative to the neighboring signal levels.

Next, the operation in the light scattering object detection mode will be described.

When rain drops are on the sensing surface 110, light travels in the light scattering object detection mode in the same manner as in FIG. 2B in Embodiment 1, in which the rain drops have poor light scattering properties so that light scattering does not occur in principle, and thus irradiation light escapes to the outside. Therefore, in principle, light is not received by the corresponding light-receiving element of the light-receiving element portion 50a. Therefore, the photo detection signal of each light-receiving element has a low signal level, regardless of the presence or the absence of the object of the rain drops. The signal pattern in this case is shown in the lower signal pattern of FIG. 13A. In this example, there are three portions in which a rain drop is attached on the sensing surface 110, but the signal pattern obtained in the light scattering object detection mode is low and flat, as seen in the lower signal pattern of FIG. 13A, and thus "no change in the signal level pattern" is detected.

The object-estimating portion 60a estimates that the object is removed from the sensing surface, when a change from "the presence of a signal pattern drop portion" to "no change in the signal pattern" is detected in the object detection mode. This estimation corresponds to (2) of FIG. 19.

Next, the detection of the presence of an object and the detection of the kind of the object in the operation in the object detection mode and the light scattering object detection mode when three spots of muddy water are present on the sensing surface 110 will be described.

When muddy water is on the sensing surface 110, light travels in the object detection mode in the same manner as in FIG. 3A in Embodiment 1, in which the total reflection condition is not satisfied on the sensing surface 110 because of the presence of the muddy water 120a on the sensing surface 110, and irradiation light escapes to the outside or is scattered. Therefore, in principle, light is not received by the light-receiving element portion 50a. However, a part of the scattered light due to light scattering of the muddy water 120a may be received, but that is far smaller than when the totally reflected light is received. Therefore, in the corresponding portion of the signal pattern, a drop portion of the signal level relative to the neighboring signal levels is detected. This case is shown in the upper signal pattern of FIG. 13B. As shown in the upper signal pattern of FIG. 13B, there are three pattern portions in which the signal level drops relative to the neighboring signal levels.

Next, the operation in the light scattering object detection mode will be described.

When muddy water is attached on the sensing surface 110, light travels in the light scattering object detection mode in the same manner as in FIG. 3B in Embodiment 1, in which when light from the light source for scattering falls on the object, which is muddy water 120a, then light scattering occurs because the muddy water 120a has light scattering properties. Therefore, scattered light is released from the muddy water 120a to the surroundings, and a part thereof is received by the light-receiving element portion 50a via the prism 30c and the lens 40a. Therefore, the photo detection signal received by the micro-light-receiving element corresponding to the sensing surface where muddy water is attached is relatively large. Consequently, in the corresponding portion in the signal pattern, the portion in which the signal level increases relatively to the neighboring signal levels is detected in the signal pattern. This case is shown in the lower signal pattern of FIG. 13B. As shown in the lower signal pattern of FIG. 13B, there are three pattern portions in which the signal level increases relative to the neighboring signals.

The object-estimating portion 60a estimates the presence of muddy water, that is, the presence of an object having light scattering properties, when "the presence of a signal pattern drop portion" is obtained in the object detection mode and "the presence of a signal pattern increase portion" is obtained in the light scattering object detection mode. This estimation corresponds to (3) and (4) of FIG. 19. A distinction whether the state is muddy water having a water content or dry mud will be described later in Embodiment 4.

The object-estimating portion 60a estimates that the light scattering object such as muddy water is removed from the sensing surface, when a change from "the presence of a signal pattern drop portion" to "no change in a signal pattern" is detected in the object detection mode, and a change from "the presence of a signal pattern increase portion" to "no change in a signal pattern" is detected in the light scattering detection mode.

Figure 14:
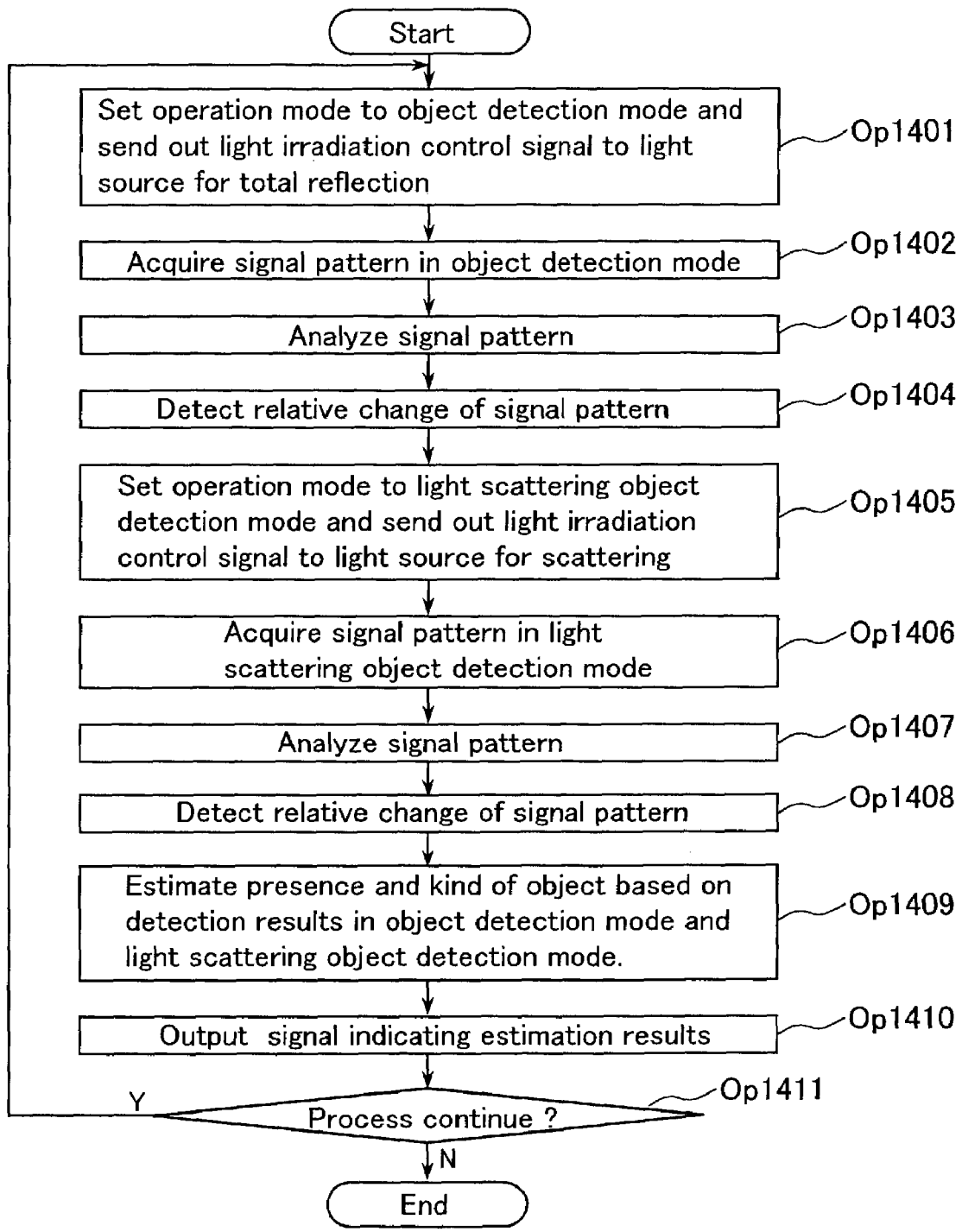
FIG. 14 is a flowchart showing a process for estimating the presence of an object, the kind of the object and the state of the object with an object-estimating portion 60a of the second object-sensing device of the present invention according to Embodiment 3.

FIG. 14 is a flowchart showing a process for estimating the presence of an object, the kind of the object and the state of the object by the object-estimating portion 60a of the object-sensing device of the present invention.

The object-estimating portion 60a sets the operation mode to the object detection mode and sends out a light irradiation control signal to the light source 10a for total reflection (operation Op 1401). The light source 10 for total reflection irradiates irradiation light onto the sensing surface 110, and the light-receiving element portion 50, which is a light receiver, receives reflected light from the sensing surface 110.

Next, the object-estimating portion 60a acquires a signal pattern in the object detection mode based on the signal level obtained from the light-receiving elements of the light-receiving element portion 50a (operation Op 1402).

Next, the object-estimating portion 60a analyzes the signal pattern and detects a change thereof (operation Op 1403).

The object-estimating portion 60a detects either one of "the presence of a signal pattern drop portion", "the presence of a signal pattern increase portion", and "no change in the signal pattern" with respect to a relative change of the signal pattern (operation Op 1404). For example, in the example of rain drops, "the presence of a signal pattern drop portion" is detected based on the signal pattern (the upper signal pattern of FIG. 13A).

Next, the object-estimating portion 60a sets the operation mode to the light scattering object detection mode and sends out a light irradiation control signal to the light source 20a for scattering (step 1405). The light source 20a for scattering irradiates irradiation light onto the sensing surface 110, and the light-receiving element portion 50a, which is a light receiver, receives scattered light from the sensing surface 110.

Next, the object-estimating portion 60a acquires a signal pattern in the light scattering object detection mode, based on the signal level of the light-receiving elements of the light-receiving element portion 50a (operation Op 1406).

Next, the object-estimating portion 60a analyzes the signal pattern and detects a change thereof (operation Op 1407).

The object-estimating portion 60a detects either one of "the presence of a signal pattern drop portion", "the presence of a signal pattern increase portion", and "no change in the signal pattern" with respect to a relative change of the signal pattern (operation Op 1408). For example, in the example of rain drops, "no change in the signal pattern portion" is detected based on the signal pattern (the lower signal pattern of FIG. 13A).

Next, the object-estimating portion 60a estimates the presence of an object and the kind of the object based on the table shown in FIG. 19, in accordance with a combination of either one of the three states of "the presence of a signal pattern drop portion", "the presence of a signal pattern increase portion" and "no change in the signal pattern" detected in the object detection mode in operation Op 1404 and either one of the three states of "the presence of a signal pattern drop portion", "the presence of a signal pattern increase portion" and "no change in the signal pattern" detected in the light scattering object detection mode in operation Op 1408 (operation Op 1409). For example, the example of rain drops corresponds to (2) of FIG. 19, so that it is estimated that rain drops are attached, and the example of muddy water corresponds to (3) or (4) of FIG. 19, so that it is estimated that muddy water is attached.

The analysis of the signal pattern of the object-estimating portion 60a makes it possible to approximately estimate the size of attached water drops. The width of the portion of the signal pattern in which the signal level drops is changed corresponding to the size of an attached water drop, so that it is possible to approximately estimate the size of an attached water drop, based on the width of the signal level drop portion of the signal pattern.

As described above, the second object-sensing device of the present invention according to Embodiment 3 can estimate the presence, the kind and the state of an object, based on a relative change in the signal pattern by analyzing a signal pattern of a photo detection signal obtained corresponding to the light-receiving element array structure. Since a relative change between micro-sections of the signal pattern is analyzed, the presence of a fine object can be detected with high precision, and the detection hardly is affected by a change in the surroundings due to the temperature characteristics.

(Embodiment 4)

As a second object-sensing device of the present invention according to Embodiment 4, an example in which an additional application function is provided for the process for estimating the kind and the state of an object will be described. In particular, in this embodiment, it is estimated whether muddy water is in the state of so-called "muddy water" having a water content or in a dry state in distinction from each other when the object is muddy water, for example.

The device configuration and the arrangement of the components can be the same as in Embodiment 3, so that the description thereof is omitted. The process of the object-estimating portion 60a is different.

First, the principle of estimating whether muddy water is in the state of so-called "muddy water" having a water content or it is dry mud in distinction with each other will be described.

The so-called "muddy water" having a water content will not be described in detail, because it is described in Embodiment 3. The path of light in the object detection mode is the same as in FIG. 2A, and the signal pattern can be detected in the same manner as in the upper signal pattern of FIG. 13B. If there are three spots of muddy water on the sensing surface, there are three portions in which the signal level drops relative to the neighboring signal levels in the signal pattern. Furthermore, the path of light in the light scattering object detection mode is the same as in FIG. 3B, and the signal pattern can be detected in the same manner as in the lower signal pattern of FIG. 13B. If there are three spots of muddy water on the sensing surface, there are three portions in which the signal level increases relative to the neighboring signal levels in the signal pattern.

Furthermore, the state of dry mud, the path of light in the object detection mode and the path of light in the light scattering object detection mode in the case where dry mud is attached are the same as those in FIG. 6 described in Embodiment 2. Although the photo detection signal level received by the micro-light-receiving element corresponding to dry mud on the sensing surface 110 drops, this drop is relatively smaller than when muddy water having a water content is attached. Thus, if dry mud is attached, there is a portion in which the signal level drops relatively to the neighboring signal levels in the signal pattern in the object detection mode.

Figures 15A, 15B:
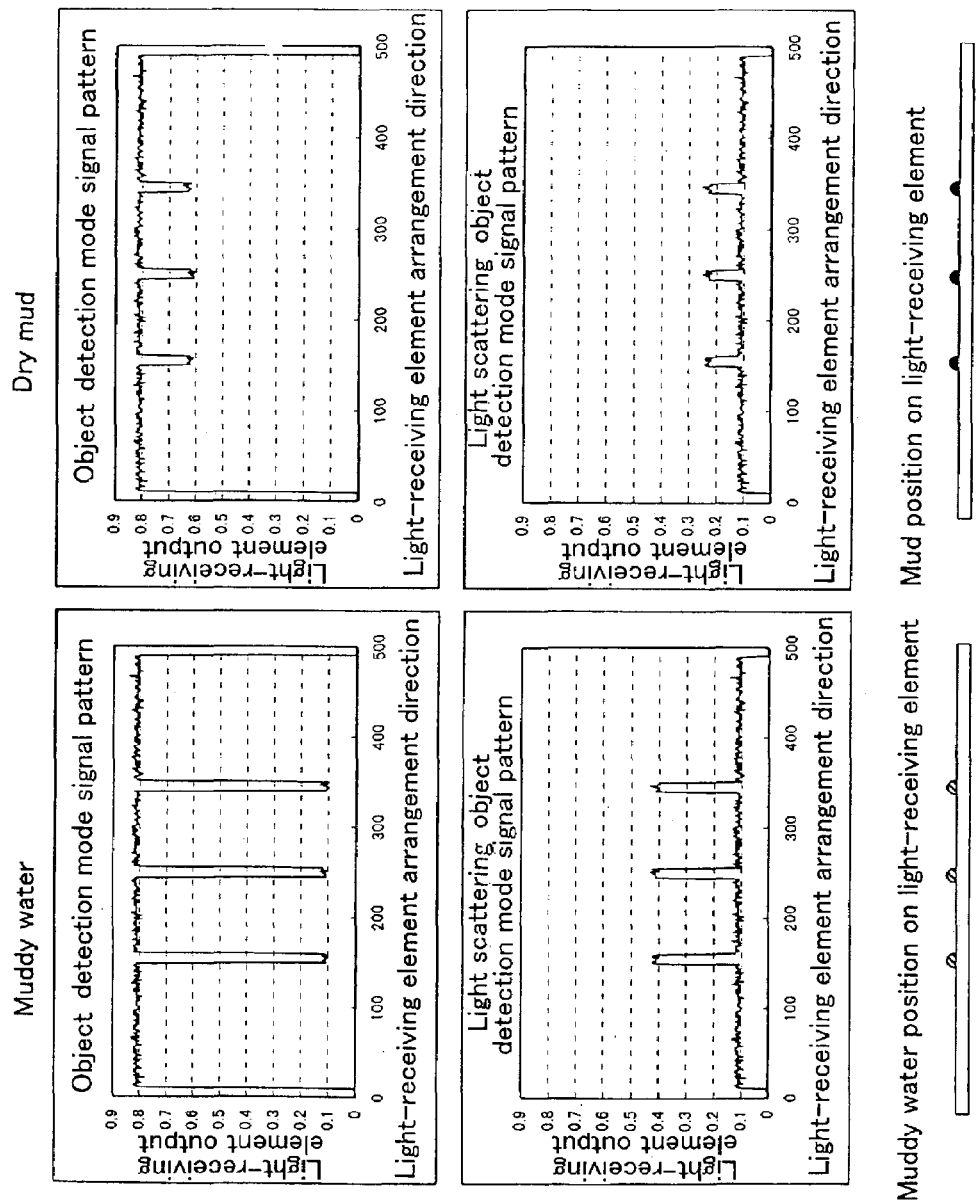
FIG. 15 is a signal pattern when the object detected by the second object-sensing device of the present invention is muddy water and dry mud.

FIG. 15 shows an example of signal patterns in the case where muddy water has a water content (A) and the case where mud is dry (B). The upper patterns are the signal patterns in the object detection mode, and the lower patterns are the signal patterns in the light scattering object detection mode. The object-sensing device of Embodiment 4 estimates the amount of the water content of an object, that is, whether it is muddy water having a water content or dry muddy water, in principle, by analyzing the signal pattern in the light scattering object detection mode. In other words, it is sufficient to evaluate the height of the waveform of the top portion in the signal pattern in FIGS. 15A and 15B. One method for increasing the estimation precision is such that a flat portion (signal pattern in a portion without an object) is taken as 100 in the two modes, and a relative magnitude of a change portion (signal pattern in a portion with an object) is evaluated. When the ratio of the magnitude of a change in the signal pattern is larger than a predetermined value, the object is estimated to be muddy water, and when it is smaller than a predetermined value, the object is estimated to be dry mud.

There is another method as follows. The signal pattern in the object detection mode is superimposed on the signal pattern in the light scattering object detection mode, and a difference in height of the signal pattern in the signal pattern portion without an object is compared with a difference in height of the signal pattern in the signal pattern portion with an object, so that the radio of the magnitude of a change in the signal pattern is evaluated quantitatively.

The process step by the object-estimating portion 60a can have the same flow as in FIG. 14. In Embodiment 4, the state detected in the object detection mode in the operation Op 1404 and the state detected in the light scattering object detection mode in the operation Op 1408 include five states of "the presence of a signal pattern drop portion (large drop ratio)", "the presence of a signal pattern drop portion (small drop ratio)", "the presence of a signal pattern increase portion (large increase ratio)", "the presence of a signal pattern increase portion (small increase ratio)" and "no change in the signal pattern". In accordance with a combination of either one of these states, the process for estimating the presence of an object and the kind of the object in the operation Op 1409 is performed based on the table shown in FIG. 19. Muddy water corresponds to the case of (3) of the table of FIG. 19, and in this case, it is estimated that muddy water is attached. On the other hand, dry mud corresponds to the case of (4) of the table of FIG. 19, and in this case, it is estimated that dry mud is attached.

As described above, according to the second object-sensing device of the present invention according to Embodiment 4, a signal pattern of a photo detection signal obtained corresponding to the light-receiving element array structure is analyzed, and it can be estimated whether the object is muddy water or dry mud, based on a relative change in the signal pattern. Since a relative change between micro-sections of the signal pattern is analyzed, the presence of a fine object can be detected with high precision, and the detection hardly is affected by a change in the surroundings due to the temperature characteristics or the like.

(Embodiment 5)

An object-sensing device of Embodiment 5 estimates whether or not there are condensed water droplets, that is, whether or not there is fogging, on the sensing surface.

The device configuration and the arrangement of the components can be the same as those in Embodiment 3 and therefore will not be described here.

The signal patterns that can be obtained in the object detection mode and the light scattering object detection mode when there are condensed water droplets on the sensing surface 110, that is, fogging on the sensing surface 110 will be described. The object-sensing device of the present invention employs the micro-array structure in each component, and the signal level of a photo detection signal detected corresponding to the object state on the sensing surface 110 is obtained as a pattern. The size of a condensed water droplet that causes fogging is far smaller than that of one light-receiving element of the object-sensing device of the present invention. Furthermore, in general, it seems that fogging due to condensation occurs not locally on the sensing surface, but occurs entirely at least on the sensing surface. Therefore, the object state is similar across the entire sensing surface 110, so that a relative change portion does not occur in the signal pattern. However, total reflection of irradiation light from a light source for total reflection and scattering of irradiation light from a light source for scattering also occur in water droplets produced by condensation, so that the signal pattern drops or increases as a whole.

However, some portions are covered with water droplets due to condensation and other are not covered therewith, and therefore in the object detection mode, the signal pattern drops as a whole, but the drop ratio is smaller than in the case where rain drops are attached. In the light scattering object detection mode, the signal pattern increases as a whole, but the increase ratio is smaller than in the case where muddy water is attached.

Figures 16A, 16B:
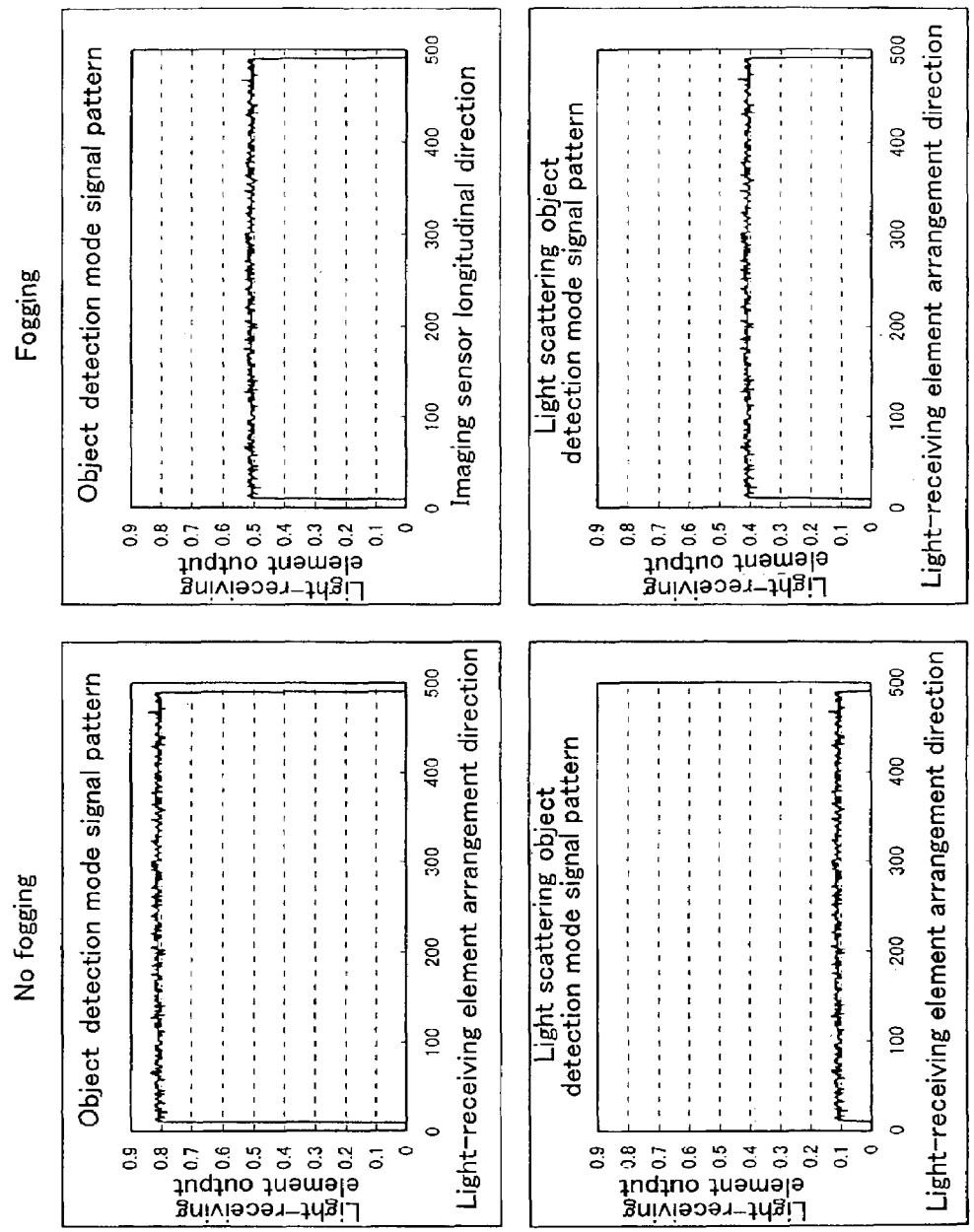
FIG. 16 is a graph showing examples of signal patterns when there is no fogging and when there is fogging because of condensation detected by the second object-sensing device of the present invention.

FIG. 16A is a signal pattern in the case where there is no fogging due to condensation. FIG. 16B is a signal pattern in the case where there is fogging due to condensation.

The upper signal pattern of FIG. 16B in the object detection mode is lower as a whole than the upper signal pattern of FIG. 16A, and is smooth and flat.

The lower signal pattern of FIG. 16B in the light scattering object detection mode is higher as a whole than the lower signal pattern of FIG. 16A, and is smooth and flat.

In short, it can be detected whether or not there is fogging due to condensation on the sensing surface by determining which of FIG. 16A and FIG. 16B the obtained signal pattern corresponds to. In this case, the two signal patterns are smooth and flat, so that determination is difficult only with the signal pattern geometry. Therefore, it is preferable to provide a mode in which all the light source 10a for total reflection and the light source 20a for scattering are turned off. If so-called "0" signal pattern based on the signal pattern obtained in this all-off mode is compared with the signal pattern obtained in the light scattering object detection mode, that makes it clear that the signal pattern obtained in the light scattering object mode increases as a whole. If light scattering occurs on the sensing surface. 110, and the signal pattern is flat, then it can be estimated that water droplets due to condensation are attached, that is, fogging occurs.

Figure 17:
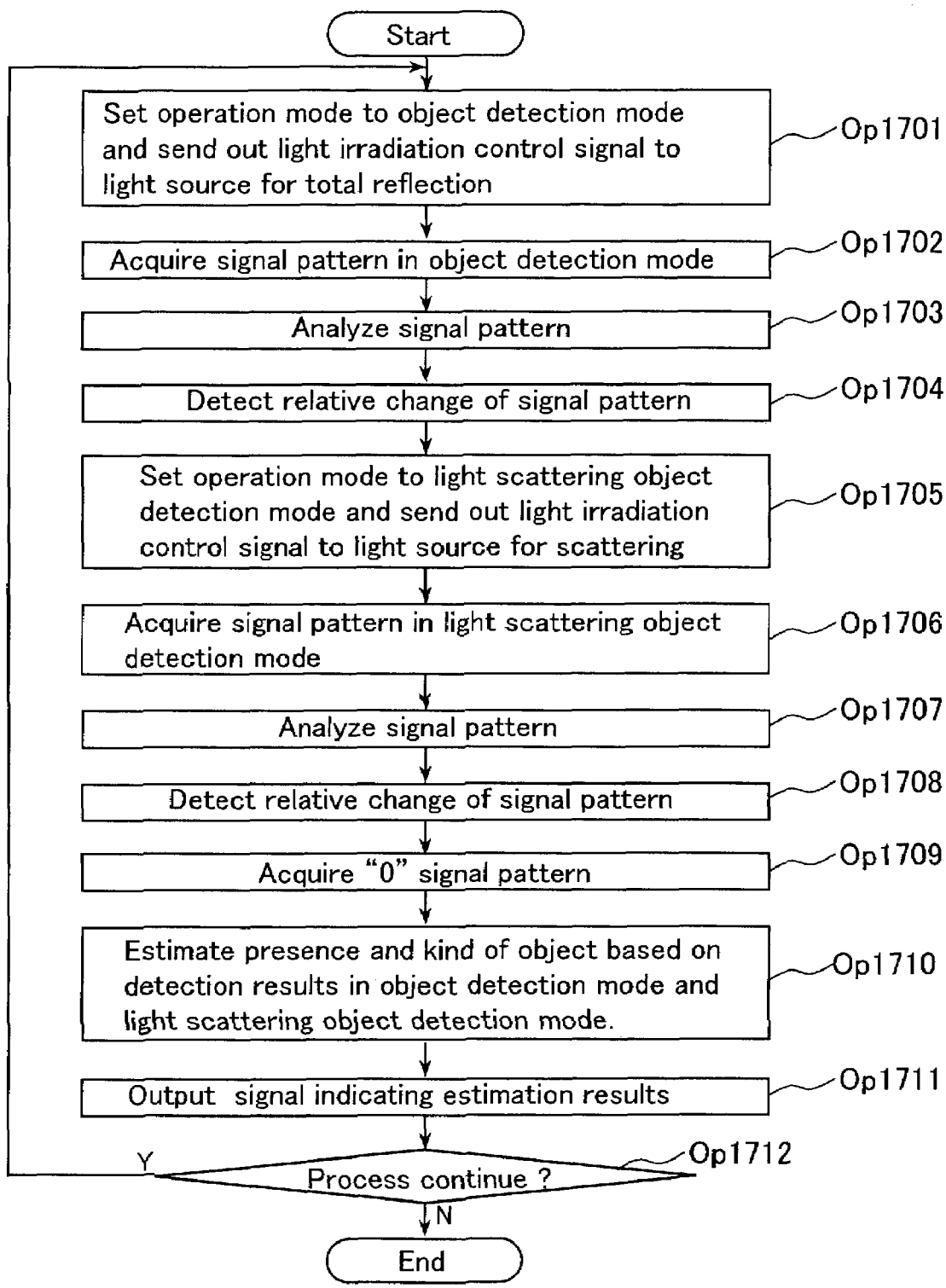
FIG. 17 is a flowchart showing a process for estimating the presence of an object, the kind of the object and the state of the object with an object-estimating portion 60a of the second object-sensing device of the present invention according to Embodiment 5.

FIG. 17 is a process step by the object-estimating portion 60a. The operations Op 1701 to 1708 of FIG. 17 can be the same as the operations Op 1401 to 1408 of FIG. 14. In Embodiment 5, "no change in the signal pattern" is detected in the object detection mode in the operation Op 1704, and "no change in the signal pattern" is detected in the light scattering object detection mode in the operation Op 1708.

Next, the light source 10a for total reflection and the light source 20a for scattering are turned off, and a photo detection signal pattern, that is, "0" signal pattern is acquired (operation Op 1709). Then, the signal pattern acquired in the light scattering object mode at operation Op 1706 is compared with the "0" signal pattern acquired in operation Op 1709, so as to detect whether or not the signal level has increased in the light scattering object mode (operation Op 1710). Next, in the object-estimating portion 60, an object is estimated based on the table shown in FIG. 19 (operation Op 1711). This case corresponds to (5) of FIG. 19 and therefore it is estimated that fogging due to condensation is attached.

The second object-sensing device of the present invention according to Embodiment 5 analyzes the signal pattern of a photo detection signal obtained corresponding to the micro-array structure and compares a relative change in the signal pattern and the "0" signal pattern so as to estimate whether or not the sensing surface fogs because of condensation.

(Embodiment 6)

The second object-sensing device of the present invention according to Embodiment 6 estimates whether or not ice is present on the sensing surface.

The device configuration and the arrangement of the components can be the same as those in Embodiment 3 and therefore will not be described here.

The signal patterns that can be obtained in the object detection mode and in the light scattering object detection mode when there is ice on the sensing surface 110 will be described.

In general, when the outside temperature is lower than the freezing temperature, some water content such as moisture in the air is solidified, and thus ice is produced. In general, it seems that freezing occurs not locally on the sensing surface, but occurs entirely at least on the sensing surface 110. Therefore, the entire signal pattern can be affected by the ice deposition.

In the case of fogging due to condensation described in Embodiment 5, water droplets are attached uniformly, so that a relative change portion is not created in the signal pattern. However, in the case of ice, the object state on the sensing surface 110 is changed irregularly because of a difference in the manner of deposition of ice crystal or a difference in a fine surface shape of ice crystal. Therefore, irregular change portions appear throughout the signal pattern.

Figures 18A, 18B:
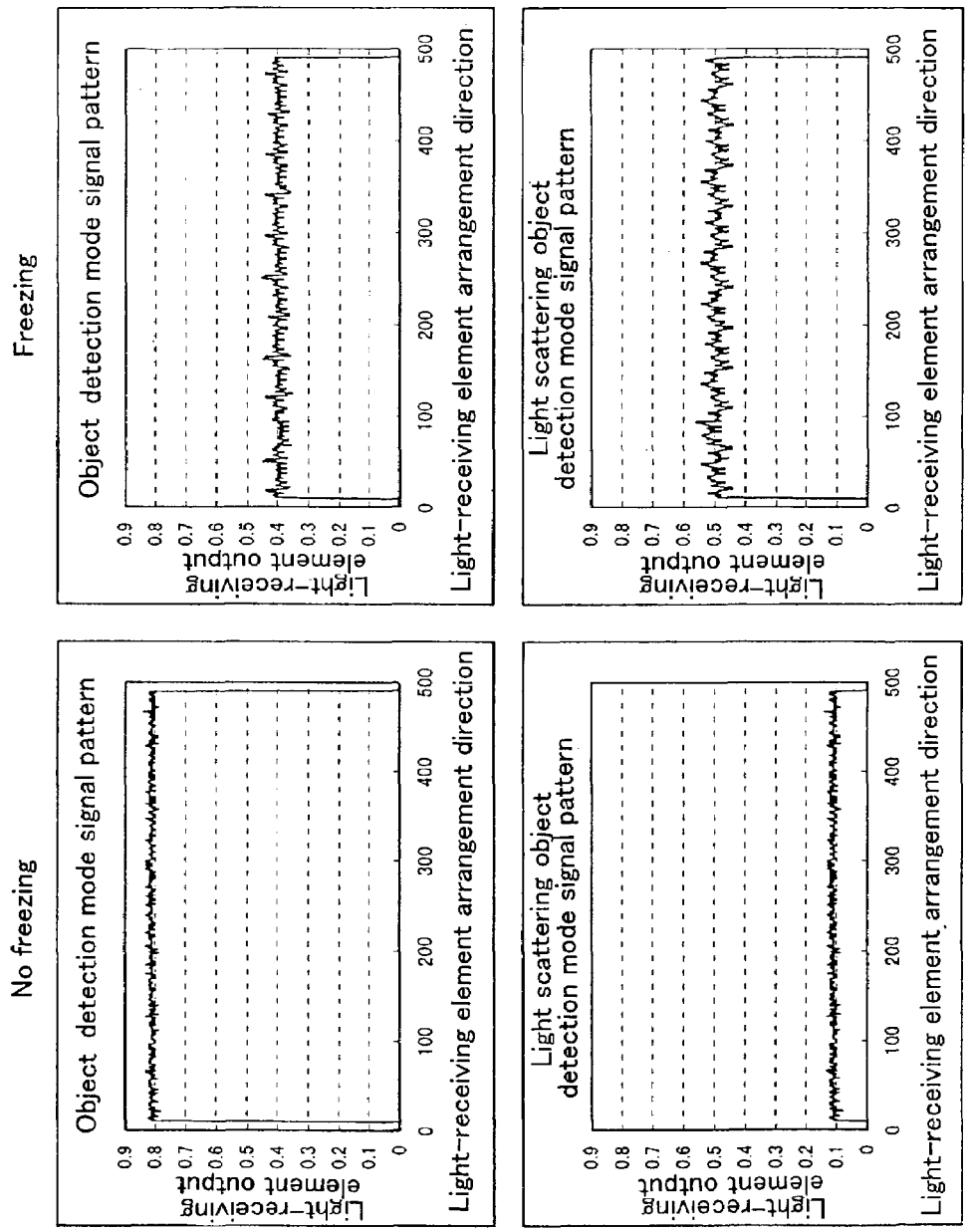
FIG. 18 is a graph showing signal patterns when there is no frozen ice and when there is frozen ice detected by the second object-sensing device of the present invention according to Embodiment 6.

FIG. 18A is a graph showing a signal pattern in the case where there is no ice. FIG. 18B is a graph showing a signal pattern in the case where there is ice. In FIGS. 18A and 18B, the upper signal pattern is one obtained in the object detection mode, and the lower signal pattern is one obtained in the light scattering object detection mode. As seen in FIG. 18B, in the case where there is ice, the signal level drops as a whole in the object detection mode, and furthermore irregular change can be seen throughout the signal pattern. In the light scattering object detection mode, the signal level increases as a whole, and furthermore irregular change can be seen throughout the signal pattern.

In short, it can be detected whether or not there is ice on the sensing surface by determining which of FIG. 18A and FIG. 18B the obtained signal pattern corresponds to. In this case, determination can be performed by evaluating the signal level and its irregularity The estimation process step by the object-estimating portion 60a of Embodiment 6 is the same as that shown in FIG. 14, but in Embodiment 6, "the presence of signal pattern irregular changes" is detected in the object detection mode in the operation Op 1404, and "the presence of signal pattern irregular changes" is detected in the light scattering object detection mode in the operation Op 1408.

In the object estimation process of the object-estimating portion 60a at operation Op 1409, this case corresponds to (6) of FIG. 19 and therefore it is estimated that ice is attached.

The second object-sensing device of the present invention according to Embodiment 6 analyzes the signal pattern of a photo detection signal obtained corresponding to the microarray structure so as to estimate the presence of ice on the sensing surface, based on a relative change in the signal pattern.

(Embodiment 7)

Embodiment 7 is an example of a device configuration of a windshield wiper control device employing the object-sensing device as a rain sensor as one embodiment of a control device using the object-sensing device of the present invention.

Figure 20:
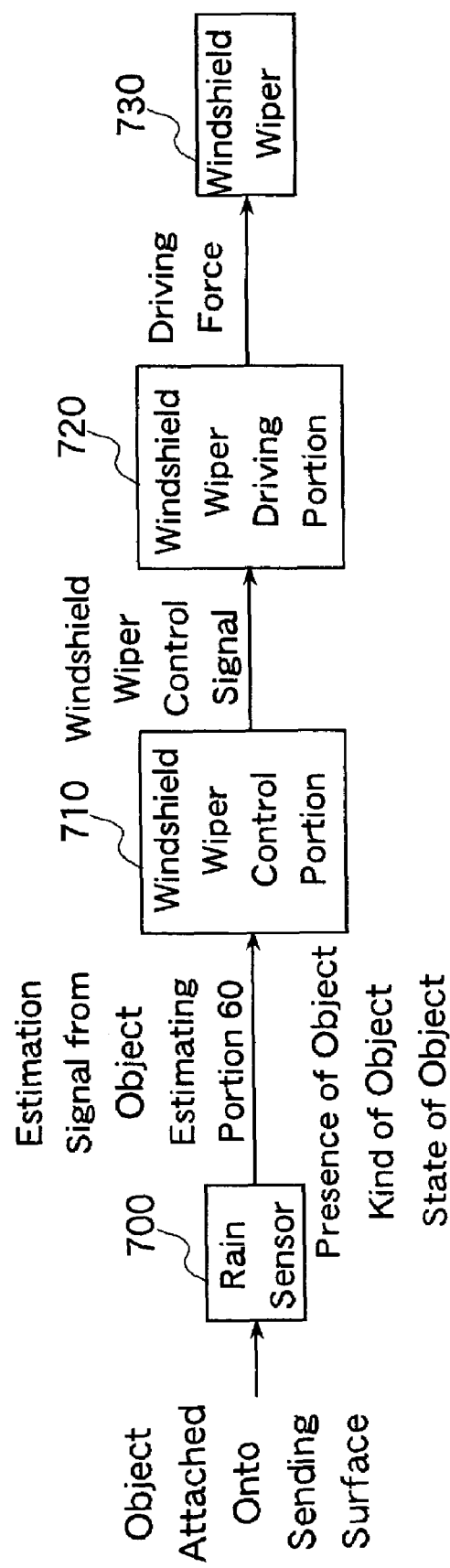
FIG. 20 is a block diagram of a windshield wiper control device using the object-sensing device of the present invention as a rain sensor.
Figure 21:
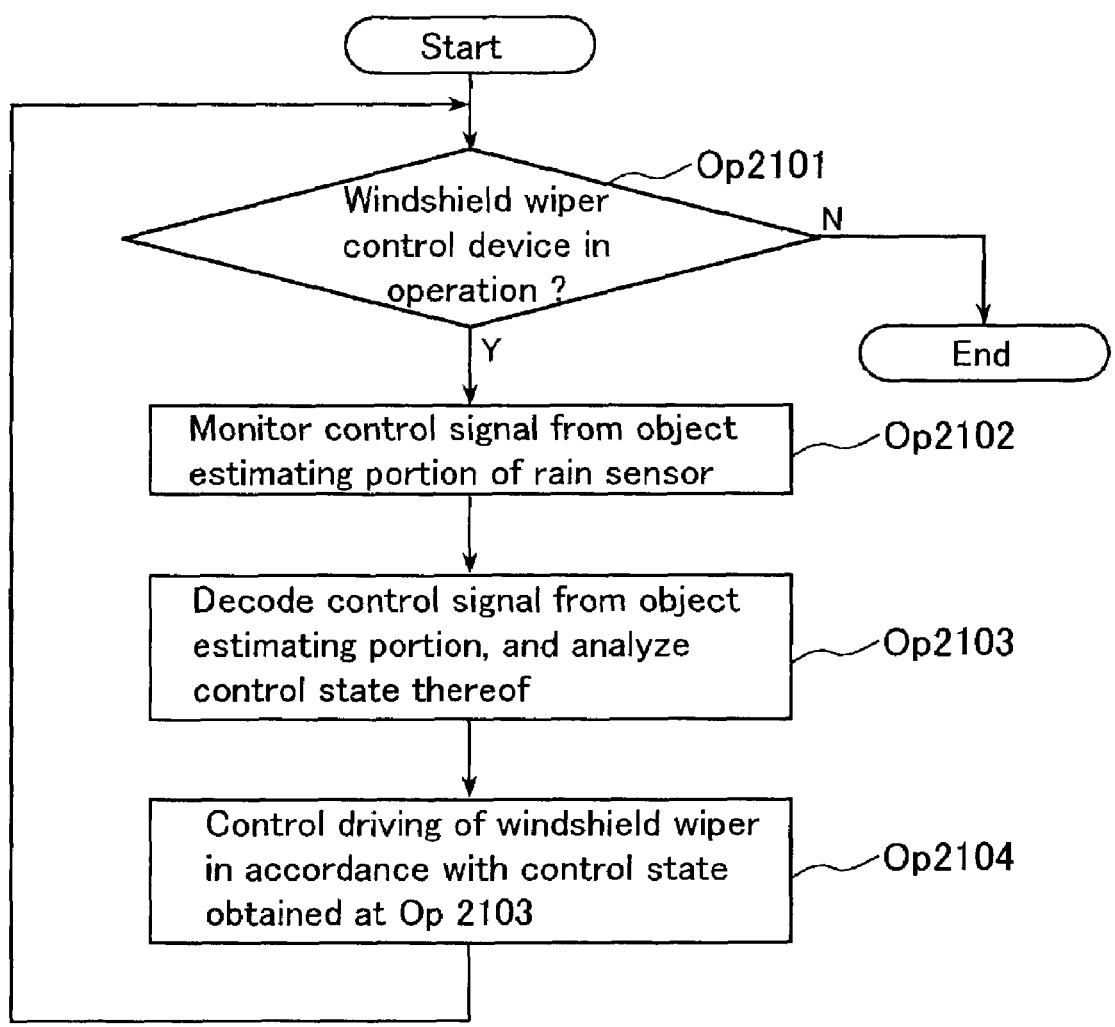
FIG. 21 is a flowchart showing an example of a flow of a process operation of the windshield wiper control device using the object-sensing device of the present invention as a rain sensor.

FIG. 20 is a block diagram of the windshield wiper control device employing the object-sensing device as a rain sensor. Reference numeral 700 denotes a functional block of the rain sensor, which is the object-sensing device of the present invention described in Embodiments 1 to 6. Reference numeral 710 denotes a windshield wiper controller. Reference numeral 720 denotes a windshield wiper driver. Reference numeral 730 denotes a windshield wiper. These components are connected as shown in FIG. 20. FIG. 21 is a flowchart showing an example of the flow of the process operation of the windshield wiper control device of Embodiment 7.

In the rain sensor 700, the angle at which the components are provided and the material of the components have been selected are as described in Embodiment 1, and a photo detection signal is output from each light-receiving element to detect a rain drop from rainfall. The object-estimating portion of the object-sensing device used as the rain sensor can perform either one of the estimation process of rain drop estimation, muddy water estimation, estimation of muddy water having a water content, estimation of dry muddy water, fogging estimation, and ice estimation processes or all the estimation processes.

The rain sensor 700 outputs six kinds of detection signals such as a "no object" estimation signal, a "a rain drop" estimation signal, "muddy water having a water content" estimation signal, a "dry muddy water" estimation signal, a "water droplets in a foggy state" estimation signal, and a "water droplets in an ice state" estimation signal.

The windshield wiper controller 710 receives the various estimation signals from the object-estimating portion of the rain sensor 700, and outputs wiper control signals in accordance with each estimation state of the surface of the windshield to the windshield wiper driver 720.

For example, a control signal to stop the wiper is output with respect to the "no object" estimation signal.

A control signal to drive the wiper is output with respect to the "a rain drop" estimation signal and the "water droplets in a foggy state" estimation signal.

A control signal to eject a cleaning agent and drive the wiper is output with respect to the "muddy water having a water content" estimation signal. Seemingly, it is preferable to wipe muddy water with a wiper together with a cleaning agent.

A control signal to stop the wiper is output with respect to the "dry muddy water" estimation signal. When dry muddy water is on the windshield, if it is wiped with the wiper as it is, the wiper control device and the windshield may be damaged. Alternatively, the control can be such that a warning that dry muddy water is present is issued to a driver. In this case, a warning indication control signal is output with respect to a control portion for controlling a warning to a driver.

A control signal to stop the wiper is output with respect to the "water droplets in an ice state" estimation signal. When water droplets in an ice state are on the windshield, if it is wiped with the wiper as it is, the wiper control device and the windshield may be damaged. Alternatively, the control can be such that a freezing prevention function incorporated in the windshield can be turned on automatically. In this case, a driving control signal is output with respect to a control portion for controlling the freezing prevention function.

The windshield wiper driver 720 receives a control signal from the windshield wiper controller 710 so as to control the driving of the windshield wiper 730.

The windshield wiper 730 is supplied with a torque by the windshield wiper driver 720 so as to be driven and put in a stop state or a driven state. The driven state includes a plurality of states that have a short or long pitch of intermittent driving. In the driven state, the predetermined surface on the windshield is wiped.

Referring to the flowchart of FIG. 21, the flow of the process operation of the windshield wiper control device will be described below.

When the windshield wiper control device is in operation (operation Op 2101: Y), the windshield wiper controller 710 monitors a control signal from the object-estimating portion 60 of the rain sensor 700 (operation Op 2102).

The windshield wiper controller 710 decodes the control signal from the object-estimating portion 60, and analyzes the control method (operation Op 2103).

The windshield wiper controller 710 controls the driving of the windshield wiper 730 in accordance with the control method obtained at the operation Op 2103 (operation Op 2104). After the operation Op 2104, the process goes to the operation Op 2101 again to form a loop and continues control (return to operation Op 2101).

Figure 22:
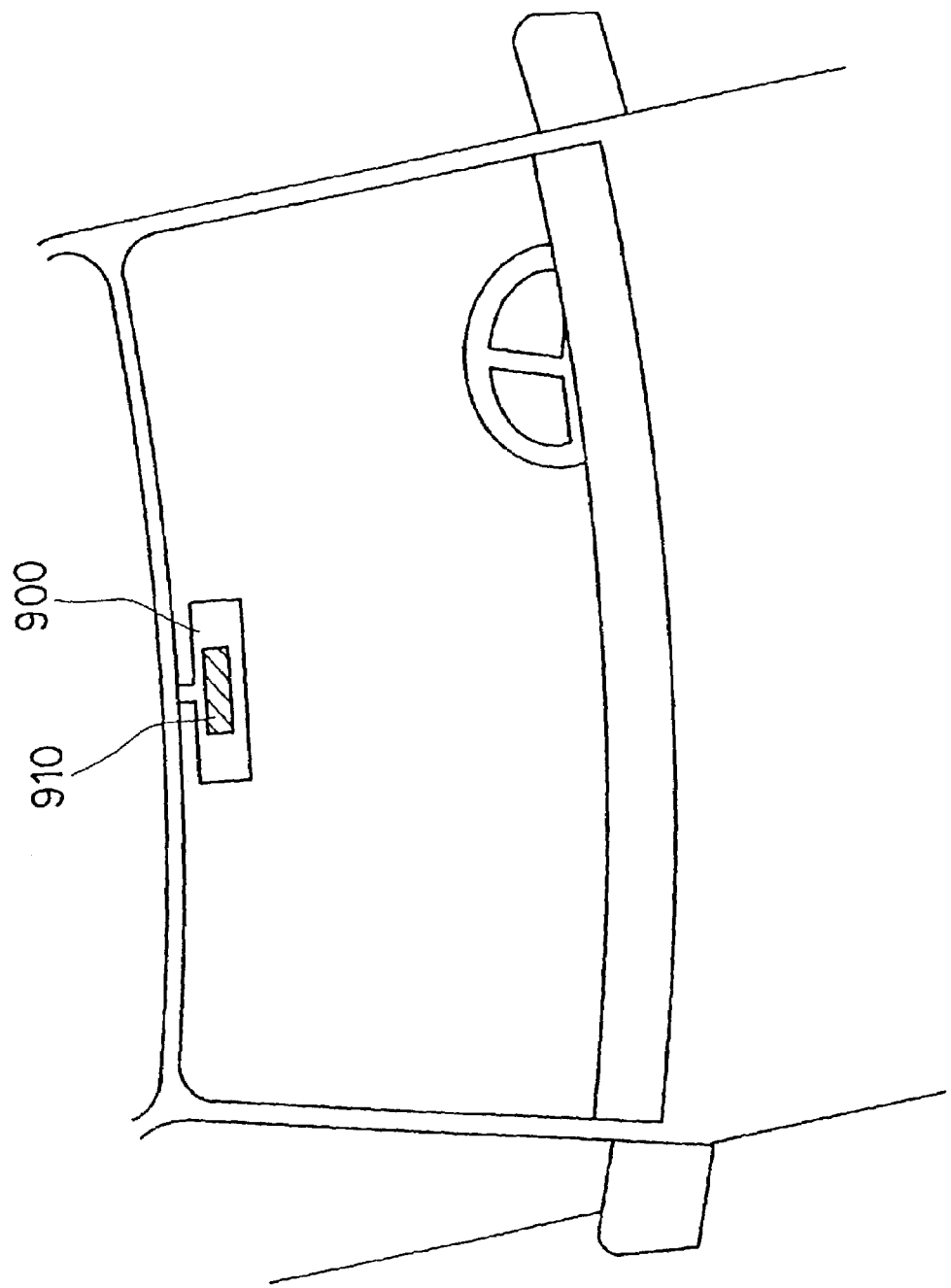
FIG. 22 is a basic view showing an example of a configuration in which the windshield wiper control device using the object-sensing device of the present invention as a rain sensor is provided.
Figure 23:
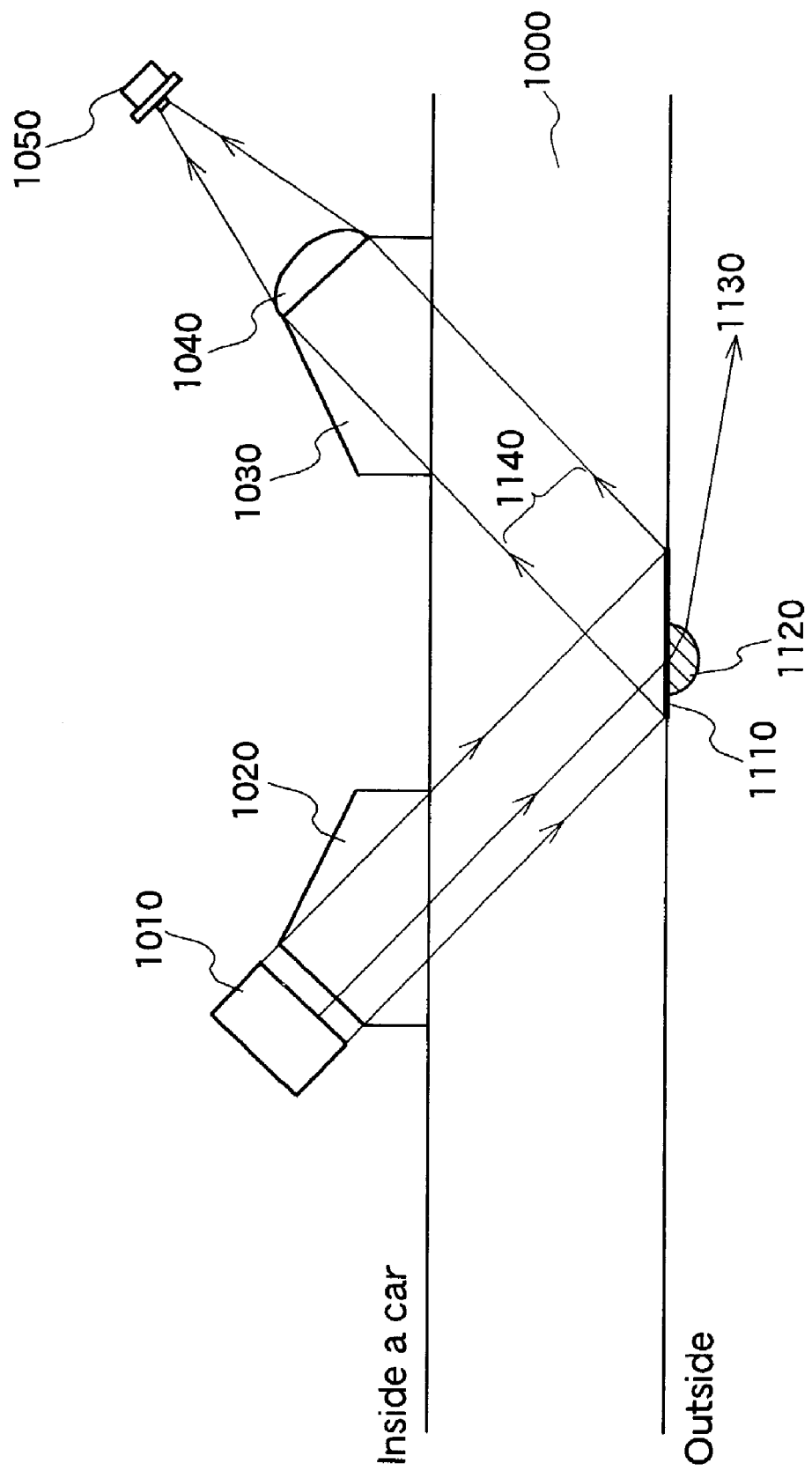
FIG. 23 is a basic view illustrating the principle of rain drop detection with a conventional reflected light sensing type rain sensor.

FIG. 22 is a view showing a basic configuration example in which the windshield wiper control device employing the object-sensing device of the present invention as a rain sensor is provided. As shown in FIG. 22, the rain sensor 700, which is the object-sensing device, is provided in a windshield portion 910 located at the back surface of a rearview mirror 900 of an automobile. When the windshield portion 910 is provided at the back surface of the rearview mirror 900 in this manner, the driving view of a driver is not unnecessarily shielded and the sensing surface can be obtained on the windshield. Although the windshield wiper controller 710 and the windshield wiper driver 720 are not shown, they are housed in a cabin as a car-equipped component near the windshield wiper 730.

The control device employing the object-sensing device shown in Embodiment 7 as described above is illustrative and the object-sensing device of the present invention is not limited to the above-described specific device configuration examples, and other device configurations can be created based on the technical idea of the present invention. The present invention can be used for applications other than the windshield wiper control device.

INDUSTRIAL APPLICABILITY

According to the first and second object-sensing devices of the present invention, the presence of an object on a sensing surface, the kind of the object and the state of the object can be estimated. For example, an object such as rain drops, muddy water having a water content, dry muddy water, water droplets in a foggy state, and water droplets in an ice state can be estimated.

According to the second object-sensing device of the present invention, the signal pattern of a photo detection signal obtained corresponding to a micro-array structure is analyzed so as to estimate the presence, the kind and the state of an object based on a relative change in the signal pattern. Since a relative change between micro-sections of the signal pattern is analyzed, the presence of a fine object can be detected with high precision and the detection hardly is affected by a change in the surroundings due to the temperature characteristics or the like.

Furthermore, according to a control device employing the first and second object-sensing devices of the present invention, the control method can be controlled in accordance with the estimation of the presence of an object on a sensing surface, the kind of the object and the state of the object. For example, if the object-sensing device is used as a rain sensor, and the control device employing the object-sensing device is used as a wiper control device, the wiper driving state can be controlled in accordance with the estimation of the object on the windshield.

What is claimed is:

1. An object-sensing device comprising a light source for total reflection and a light source for scattering,
    wherein an outer surface of a transparent substrate is used as a sensing surface on which an incident light admitted into the transparent substrate from the light source for total reflection is reflected, and an incident light admitted into the transparent substrate from the light source for scattering is irradiated,
    the light source for total reflection, the transparent substrate and a light receiver are arranged such that the reflected light of the light source for total reflection from the sensing surface can be received by the light receiver, and the light source for scattering and the light receiver are arranged such that scattered light of the light source for scattering from the sensing surface can be received,
    the object-sensing device comprising:
    an object sensor for detecting a change due to an object in a signal level from the light source for total reflection in a photo detection signal detected by the light receiver so as to detect a presence of the object; and
    a light-scattering-object sensor for detecting a change due to an object in a signal level from the light source for scattering in a photo detection signal detected by the light receiver so as to detect whether or not the object is a light scattering object,
    wherein the light source for total reflection and the light source for scattering are switched for operation.

2. The object-sensing device according to claim 1, wherein the object sensor and the light-scattering-object sensor receive light from the same detecting surface.

3. The object-sensing device according to claim 1, wherein
    when the presence of an object is detected by the object sensor, and the presence of a light scattering object is detected by the light-scattering-object sensor, then the object is estimated to be muddy water, and
    when the presence of an object is detected by the object sensor, and the presence of a light scattering object is not detected by the light-scattering-object sensor, then the object is estimated to be a water drop.

4. The object-sensing device according to claim 1, wherein the light source for scattering and the light receiver are arranged such that scattered light from the sensing surface by the light source for scattering is received, and totally reflected light on the sensing surface is not directly incident to the light receiver in a state where there is no object on the sensing surface.

5. A window wiper device comprising:
    the object-sensing device according to claim 1 which is used as a rain sensor for detecting a presence of an object attached on a window shield of an automobile, on which the sensing surface is provided;
    a window wiper driver; and
    a window wiper controller,
    wherein the window wiper controller changes a control of the window wiper driver, based on estimation results with respect to a kind and a state of an object from the object estimating portion.

6. An object-sensing device comprising two types of light sources for total reflection and scattering,
    wherein a portion of an outer surface of a transparent substrate is used as a sensing surface on which an incident light admitted into the transparent substrate from the light source for total reflection is reflected, and an incident light admitted into the transparent substrate from the light source for scattering is irradiated, the object-sensing device comprising:

an imaging lens for forming an image with each of the reflected light by the light source for total reflection and scattered light by the light source for scattering that are incident from the sensing surface, a light source switch for switching irradiation of the light source for total reflection and irradiation of the light source for scattering; and a light-receiving element array in which a plurality of micro-light-receiving elements are arranged, wherein light from the imaging lens is received by the light-receiving element array, a signal pattern in which photo detection signals from each micro-light-receiving element are aligned in accordance with an arrangement of the micro-light-receiving elements is generated, the presence of an object is detected based on the signal pattern obtained from the irradiation of the light source for total reflection, and whether or not the object is a light scattering object is detected based on the signal pattern obtained from the irradiation of the light source for scattering.

7. The object-sensing device according to claim 6, comprising:

an object sensor for detecting that an object is present when a presence of a pattern portion in which a signal level drops relative to neighboring signal levels is detected in the signal pattern, the object being present on the sensing surface corresponding to the pattern portion; and a light-scattering-object sensor for detecting that a light scattering object is present when a presence of a pattern portion in which a signal level increases relative to neighboring signal levels is detected in the signal pattern, the light scattering object being present on the sensing surface corresponding to the pattern portion, wherein when the presence of the object is detected by the object sensor, and the presence of the light scattering object is detected by the light-scattering-object sensor, then the object is estimated to be a substance having light scattering properties, and when the presence of the object is detected by the object sensor, and the presence of the scattering object is not detected by the light-scattering-object sensor, then the object is estimated to be a substance having light transmission properties.

8. The object-sensing device according to claim 6, wherein a magnitude of the light scattering properties of the object is estimated based on a relative magnitude of a pattern portion exhibiting a relative increase from neighboring signal levels in the signal pattern of the scattered light of the light source for scattering that is detected by the light-scattering-object sensor.

9. The object-sensing device according to claim 6, wherein a kind and a state of the object are estimated based on a relative change of a pattern portion exhibiting a relative increase from neighboring signal levels in the signal pattern of the scattered light of the light source for scattering that is detected by the light-scattering-object sensor.

10. The object-sensing device according to claim 6, wherein when a presence of an object is detected by the object sensor, and a presence of a scattering object is detected by the light-scattering-object sensor, then the object is estimated to be muddy water, and when a presence of an object is detected by the object sensor, and a presence of a scattering object is not detected by the light-scattering-object sensor, then the object is estimated to be a water drop.

11. The object detecting device according to claim 6, wherein when a presence of an object is detected by the object sensor, and a presence of a scattering object is detected by the light-scattering-object sensor, then the object is estimated to be muddy water, and a relative magnitude of a pattern portion exhibiting a relative increase of a signal level from neighboring signal levels in the signal pattern of the scattered light of the light source for scattering that is detected by the light-scattering-object sensor is smaller than a predetermined ratio, then it is estimated that the muddy water is dry.

12. The object-sensing device according to claim 6, wherein when in a signal pattern of the reflected light of the light source for total reflection detected by the object sensor, a signal level drop over the signal pattern is detected, and in a signal pattern of the scattered light of the light source for scattering detected by the light-scattering-object sensor, a signal level increase over the signal pattern is detected, then the object is estimated to be water droplets due to condensation.

13. The object-sensing device according to claim 6, wherein when in a signal pattern of the reflected light of the light source for total reflection detected by the object sensor, a signal level is dropped over the signal pattern and a change in the signal pattern is not smooth, and in a signal pattern of the scattered light of the light source for scattering detected by the light-scattering-object sensor, a signal level is increased over the signal pattern and a change in the signal pattern is not smooth, then the object is estimated to be ice due to freezing.

14. The object-sensing device according to claim 6, wherein the light source for scattering, the imaging lens and the light receiver are arranged such that scattered light from the sensing surface by the light source for scattering is received, and totally reflected light on the sensing surface is not directly incident to the light receiver 15. A window wiper device comprising:

the object-sensing device according to claim 6 which is used as a rain sensor for detecting a presence of an object attached on a window shield of an automobile, on which the sensing surface is provided;

a window wiper driver; and a window wiper controller, wherein the window wiper controller changes a control of the window wiper driver, based on estimation results with respect to a kind and a state of an object from the object estimating portion.

* * * * *